United States Patent
Coric

(10) Patent No.: US 12,383,619 B2
(45) Date of Patent: *Aug. 12, 2025

(54) USE OF GLUTAMATE MODULATING AGENTS WITH IMMUNOTHERAPIES TO TREAT CANCER

(71) Applicant: Biohaven Therapeutics Ltd., New Haven, CT (US)

(72) Inventor: Vladimir Coric, Madison, CT (US)

(73) Assignee: Biohaven Therapeutics Ltd., Tortola (VG)

( * ) Notice: Subject to any disclaimer, the term of this patent is extended or adjusted under 35 U.S.C. 154(b) by 651 days.

This patent is subject to a terminal disclaimer.

(21) Appl. No.: 16/302,270

(22) PCT Filed: May 19, 2017

(86) PCT No.: PCT/US2017/033690
§ 371 (c)(1),
(2) Date: Nov. 16, 2018

(87) PCT Pub. No.: WO2017/201502
PCT Pub. Date: Nov. 23, 2017

(65) Prior Publication Data
US 2019/0175731 A1  Jun. 13, 2019

Related U.S. Application Data

(60) Provisional application No. 62/339,433, filed on May 20, 2016.

(51) Int. Cl.
*A61K 39/395* (2006.01)
*A61K 31/426* (2006.01)
(Continued)

(52) U.S. Cl.
CPC ........ *A61K 39/3955* (2013.01); *A61K 31/426* (2013.01); *A61K 31/428* (2013.01);
(Continued)

(58) Field of Classification Search
None
See application file for complete search history.

(56) References Cited

U.S. PATENT DOCUMENTS

| 10,639,298 B2 * | 5/2020 | Wrobel | ............. C07K 5/06026 |
| 2015/0045401 A1 * | 2/2015 | Smith | ................... A61K 45/06 |
| | | | 514/367 |

(Continued)

FOREIGN PATENT DOCUMENTS

| WO | 2013138753 A1 | 9/2013 |
| WO | 2016073759 | * 5/2016 |

(Continued)

OTHER PUBLICATIONS

Rizvi et al., Lancet Oncol. Mar. 2015; 16(3): 257-265 (Year: 2015).*

(Continued)

*Primary Examiner* — Karl J Puttlitz

(57) ABSTRACT

Disclosed are methods of treating cancer using a combination of an immunotherapeutic agent, such as, for example, a PD-1, PD-L1 or CTLA-4 checkpoint inhibitor, and a glutamate modulating agent such as riluzole or trigriluzole. Pharmaceutical compositions and kits including the immunotherapeutic agents and glutamate modulating agents are also disclosed.

24 Claims, 2 Drawing Sheets

(51) Int. Cl.

| | |
|---|---|
| *A61K 31/428* | (2006.01) |
| *A61K 45/06* | (2006.01) |
| *A61P 35/00* | (2006.01) |
| *C07D 277/82* | (2006.01) |
| *C07K 16/28* | (2006.01) |
| *A61K 39/00* | (2006.01) |

(52) U.S. Cl.
CPC ........ *A61K 39/39566* (2013.01); *A61K 45/06* (2013.01); *A61P 35/00* (2018.01); *C07D 277/82* (2013.01); *C07K 16/2818* (2013.01); *A61K 2039/505* (2013.01); *C07K 2317/24* (2013.01)

(56) References Cited

U.S. PATENT DOCUMENTS

| | | | |
|---|---|---|---|
| 2015/0148329 A1 | | 5/2015 | Reitz et al. |
| 2021/0236470 A1* | | 8/2021 | Wrobel ............... A61P 25/00 |
| 2022/0396555 A1* | | 12/2022 | Wrobel ............... C07K 5/06104 |

FOREIGN PATENT DOCUMENTS

| | | | |
|---|---|---|---|
| WO | 2016073759 A1 | | 5/2016 |
| WO | 2016140878 | * | 9/2016 |
| WO | 2016140878 A9 | | 9/2016 |
| WO | 2016140879 | * | 9/2016 |
| WO | 2016140879 A1 | | 9/2016 |
| WO | 2016168716 A1 | | 10/2016 |
| WO | 2017059224 A1 | | 4/2017 |

OTHER PUBLICATIONS

Faghfuri et al., Expert Review of Anticancer Therapy, 15:9, 981-993, Abstract (Year: 2015).*
Rituxan (rituximab), label in formation, accessed Aug. 13, 2024 from https://www.accessdata.fda.gov/drugsatfda_docs/label/2010/103705s5311lbl.pdf (Rituximab); (Year: 2010).*
Chemotherapy of Neoplastic Diseases in Goodman & Gilman's: The Pharmacological Basis of Therapeutics, 2008 (Year: 2008).*
Chen et al. "Anti-PD-1/PD-L1 therapy of human cancer: past, present, and future" The Journal of Clinical Investigation, 2015, 125(9), 3384-3391.
McDonnell et al. "Riluzole prodrugs for melanoma and ALS: design, synthesis, and in vitro metabolic profiling" Bioorganic and Medicinal Chemistry, 2012, 20(18), 5642-5648.
Kretschmer et al. "Riluzole, a glutamate release inhibitor, and motor behavior" Archives of Pharmacology, 1998, 358, 181-190.
Sperling et al. "Riluzole: A Potential Therapeutic Intervention in Human Brain Tumor Stem-like Cells" Oncotarget, published on May 20, 2017 (13 pages).
Teh et al. "Metabotropic Glutamate Receptors and Cancerous Growth" WIREs Membrane Transport and Signaling, 2012, 1, 211-220.
Meldrum "Glutamate as a Neurotransmitter in the Brain: Review of Physiology and Pathology" The Journal of Nutrition, 2000, 1007S-1015S.
Chen et al. "Targeting Glutamine Induces Apoptosis: A Cancer Therapy Approach" International Journal of Molecular Sciences, 2015, 16, 22830-22855.
Yelamanchi et al. "A Pathway Map of Glutamate Metabolism" Journal of Cell Communication and Signaling, 2016, 10 (1), 69-75.
Hoering et al. "End Points and Statistical Considerations in Immuno-Oncology Trials: Impact on Multiple Myeloma" Future Oncology, published online on Apr. 11, 2017 (13 pages).
Ott et al. "Combination Immunotherapy: A Road Map" Journal for ImmunoTherapy of Cancer, 2017, 5:16 (15 pages).
Tirano et al. "Blockade of B7-H1 and PD-1 by Monoclonal Antibodies Potentiates Cancer Therapeutic Immunity" Cancer Research, published Feb. 2005 (13 pages).
Zeng et al. "Anti-PD-1 Blockade and Stereotactic Radiation Produce Long-Term Survival in Mice with Intracranial Gliomas" International Journal of Radiation Oncology, Biology, Physics, 2013, 86, 343-349.
International Search Report dated Oct. 10, 2017 issued for the corresponding application PCT/US2017/033690 (4 pages).
Written Opinion dated Oct. 10, 2017 issued for the corresponding application PCT/US2017/033690 (10 pages).
International Preliminary Report on Patentability dated Nov. 20, 2018 issued for the corresponding application PCT/US2017/033690 (11 pages).
Supplemental European Search Report dated Aug. 21, 2019 and Written Opinion issued for the corresponding European Patent Application No. 17800311.7 (7 pages).
International Search Report dated Aug. 10, 2017 issued for the corresponding application PCT/US2017/033688 (1 bage).
Written Opinion dated Aug. 10, 2017 issued for the corresponding application PCT/US2017/033688 (5 pages).
International Preliminary Report on Patentability dated Nov. 20, 2018 issued for the corresponding application PCT/US2017/033688 (11 pages).
Supplemental European Search Report dated Oct. 22, 2019 and Written Opinion issued for the corresponding European Patent Application No. 17800310.9 (5 pages).
Speyer et al. "Riluzole mediates anti-tumor properties in breast cancer cells independent of metabotropic glutamate receptor-1" Breast Cancer Research and Treatment, 2016, 157, 217-228.
Preusser et al. "Prospects of Immune Checkpoint Modulators in the Treatment of Glioblastoma" Nature Reviews Neurology, 2015, 11(9), 1-22.

* cited by examiner

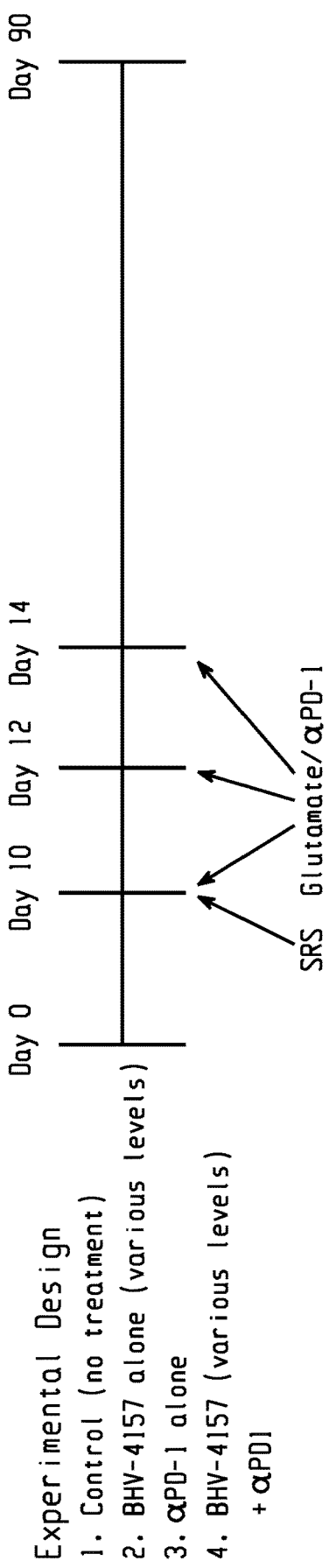

USE OF GLUTAMATE MODULATING AGENTS WITH IMMUNOTHERAPIES TO TREAT CANCER

CROSS-REFERENCE TO RELATED APPLICATIONS

This application is a Section 371 national phase filing of PCT/US2017/033690, filed May 19, 2017, which claims priority under 35 U.S.C. § 119 (e) to U.S. Provisional Application Ser. No. 62/339,433 filed May 20, 2016, both of which are incorporated by reference in their entirety.

FIELD OF THE INVENTION

The present invention relates to the use of glutamate modulating agents and immunotherapeutic anti-cancer agents in the treatment of cancer.

BACKGROUND OF THE INVENTION

Glutamate is a predominant excitatory neurotransmitter responsible for regulating signaling in normal brain function. While research on glutamate signaling has been primarily focused on the central nervous system (CNS), other investigations have highlighted their functional role in peripheral tissues. See, e.g., Skerry T, Genever P, Glutamate signalling in non-neuronal tissues. *Trends Pharmacal Sci* 2001, 22:174-181 and Frati C, Marchese C, Fisichella G, Copani A, Nasca M R, Storto M, Nicoletti F, Expression of functional mGlu5 metabotropic glutamate receptors in humanmelanocytes. *J Cell Physiol* 2000, 183:364-372.

Glutamate can exert its signaling abilities by acting on glutamate receptors, which are located on the cell surface. Glutamate receptors exist as either ionotropic receptors (iGluRs) or metabotropic glutamate receptors (mGluRs). iGluRs are ligand-gated ion channels, which include N-methyl-d-aspartate (NMDA) receptors and non-NMDA receptors [α-amino-3-hydroxy-5-methyl-4-isoxazolepropionic acid (AMPA) receptors] (iGluR1-4) and kainite (KA) subfamilies (iGluR5-7, KA1, and KA2). mGluRs are domain receptors that mediate their signal by coupling to Guanosine triphosphate (GTP)-binding proteins (G-proteins) and stimulate second messengers such as inositol 1,4,5-triphosphate (IP3), diacylglycerol (DAG), and cyclic adenosine monophosphate (cAMP). Various mGluR subtypes have been identified and grouped according to their sequence homology, pharmacologic response, and intracellular second messengers. Upon binding of the ligand, Group I receptors, which are comprised of mGluR1 and mGluR5, couple via $G_q$ to phospholipase C (PLC) leading to the formation of IP3 and DAG. Group II comprises mGluR2 and mGluR3, and Group III comprises mGluR4, mGluR6, mGluR7 and mGluR8. Both Group II and III are negatively coupled via $G_{i/o}$ to adenyl cyclase leading to cAMP formation. See, e.g., Teh J, Chen S, Metabotrobic glutamate receptors and cancerous growth, *WIREs Membr Transp Signal* 2012, 1:211-220. doi: 10.1002/wmts.21, 2011 WILEY-VCH Verlag GmbH & Co. KGaA, Weinheim. Volume 1, March/April 2012.

Glutamate can also be transported. Glutamate transporters have been cloned from the mammalian central nervous system. Two are expressed predominantly in glia [glial glutamate and aspartate transporter (GLAST) and glial glutamate transporter (GLT)] and three in neurons [EAAC1, excitatory amino acid transporter (EAAT)4 and EAAT5]. See, e.g., Seal, R, Amara, S, (1999) Excitatory amino acid transporters: a family in flux. *Annu. Rev. Pharmacol. Toxicol.* 39: 431-456. Further information concerning glutamate transport can be found in the literature. See, e.g., Meldrum B, Glutamate as a Neurotransmitter in the Brain: Review of Physiology and Pathology, *J. Nutr.* 130:1007S-1015S, 2000.

Glutamate can also be metabolized. Glutamate metabolism reactions can be catalyzed by enzymes that are regulated by activators and inhibitors. For instance, conversion of L-glutamate to N-acetyl L-glutamate in presence of N-acetylglutamate synthase (NAGS) is activated by L-arginine and inhibited by succinate, coenzyme A, N-acetyl-L-aspartate and N-acetyl-L-glutamate. See, e.g., Shigesada K, Tatibana M, N-acetylglutamate synthetase from rat-liver mitochondria. Partial purification and catalytic properties. *Eur J Biochem.* 1978; 84:285-291. doi: 10.1111/j.14321033.1978. tb12167.x. Similarly, glutamine to glutamate conversion can be catalyzed by enzymes, which include glutaminase (GLS/GLS2), phosphoribosyl pyrophosphate amidotransferase (PPAT) and glutamine-fructose-6-phosphate transaminase (GFPT1 and GFPT2). See, e.g., Holmes E, Wyngaarden J, Kelley W, Human glutamine phosphoribosylpyrophosphate amidotransferase. Two molecular forms interconvertible by purine ribonucleotides and phosphoribosylpyrophosphate. *J Biol Chem* 1973; 248: 6035-6040, and Hu C, et al. Molecular enzymology of mammalian Delta1-pyrroline-5-carboxylate synthase. Alternative Splice donor Utilization Generates Isoforms with Different Sensitivity to Ornithine Inhibition. *J Biol Chem.* 1999; 274:6754-6762. doi:10.1074/jbc.274.10.6754.

Glutamine, which serves as a precursor of glutamate is known to protect the body from nutrient depletion, oxidative stress and tumor stress. See, e.g., Shanware N, et al., Glutamine: pleiotropic roles in tumor growth and stress resistance. *J Mol Med (Berl)* 2011; 89:229-236. doi: 10.1007/s0010901107319. Reports have shown that ammonia released from glutamine by the action of glutaminases regulates autophagy in cancer cells through a process known as glutaminolysis. See, e.g., Eng C, et al., (2010) Ammonia derived from glutaminolysis is a diffusible regulator of autophagy. *Sci Signal* 3:ra31. In cancer cells, glutaminolysis may serve as a fuel for cell growth and proliferation through the synthesis of fatty acids, nucleotides and amino acids. See, e.g., Benjamin D, et al., Global profiling strategies for mapping dysregulated metabolic pathways in cancer. *Cell Metab.* 2012; 16:565-577. doi: 10.1016/j.cmet.2012.09.013. Expression of glutaminase may be regulated by the transcription factor, c-Myc, which in turn regulates cell proliferation and cell death in human prostate cancer cells. See, e.g., Gao P, et al., c-Myc suppression of miR23a/b enhances mitochondrial glutaminase expression and glutamine metabolism. *Nature.* 2009; 458:762-765. doi: 10.1038/nature07823. In brain tumors such as gliomas, it has been shown that glioma cells may release excess glutamate into the extracellular space resulting in tumor-related epilepsy or seizures. See, e.g., Simon M, von Lehe M, Glioma-related seizures: glutamate is the key. *Nat Med.* 2011; 17:1190-1191. doi: 10.1038/nm.2510. There are also suggestions that glutamate release promotes cell proliferation, cell invasion and tumor necrosis in glioblastoma. See, e.g., Schunemann D, et al., Glutamate promotes cell growth by EGFR signaling on U87MG human glioblastoma cell line. *Pathol Oncol Res.* 2010; 16:285-293. doi: 10.1007/s1225300992234. Further information concerning glutamate and glutamine metabolism can be found in the literature. See, for example, Yelamanchi S., et al., A pathway map of glutamate metabolism, *J Cell Commun Signal.* 2016 March: 10(1):69-76. Doi10.1007/s12079-015-0315-5, and Chen L and Hengmin C, Targeting Glutamine Induces Apoptosis: A Cancer Therapy Approach, *Int. J. Mol. Sci.* 2015, 16, 22830-22855; doi:10.3390/ijms160922830.

Riluzole (6-(trifluoromethoxy)benzothiazol-2-amine) is a pharmaceutical which has been used for treatment of amyotrophic lateral sclerosis (ALS). Recently, riluzole has been shown to have other clinical benefits. For example, orally administered riluzole dosed twice a day at a total dose of 100 mg per day may relieve or treat neuropsychiatric symptoms and disorders, such as mood, anxiety disorder, refractory depression, obsessive-compulsive anxiety and the like. See, e.g., Riluzole Augmentation in Treatment-refractory Obsessive-compulsive Disorder, Yale University (2016) Retrieved from https://clinicaltrials.gov/ct2 (Identification No. NCT00523718). Also, there is some indication that riluzole may have anti-cancer effects. See, e.g., Riluzole in Treating Patients With Stage III or Stage IV Melanoma That Cannot Be Removed by Surgery, Rutgers University (2013) Retrieved from https://clinicaltrials.gov/ct2 (Identification No. NCT00866840).

Human cancers harbor numerous genetic and epigenetic alterations, generating neoantigens potentially recognizable by the immune system. See, e.g., Sjoblom et al. (2006) *Science* 314:268-74). The adaptive immune system, comprised of T and B lymphocytes, has powerful anti-cancer potential, with a broad capacity and exquisite specificity to respond to diverse tumor antigens. Further, the immune system demonstrates considerable plasticity and a memory component. The successful harnessing of these attributes of the adaptive immune system makes immunotherapy unique among current cancer treatment modalities.

Cancer immunotherapy includes approaches that enhance anti-tumor immune responses by adoptive-transfer of activated effector cells, immunization against relevant antigens, or providing non-specific immune-stimulatory agents such as cytokines. Cancer immunotherapy also includes immune checkpoint pathway inhibitors that have provided new immunotherapeutic approaches for treating cancer, including, for example, inhibitors that target the Programmed Death-1 (PD-1) receptor and block the inhibitory PD-1/PD-1 ligand pathway and the Cytotoxic T-Lymphocyte Antigen-4 (CTLA-4) receptor.

PD-1 is a key immune checkpoint receptor expressed by activated T and B cells and mediates immunosuppression. PD-1 is a member of the CD28 family of receptors, which includes CD28, CTLA-4, ICOS, PD-1, and BTLA. Two cell surface glycoprotein ligands for PD-1 have been identified, Programmed Death Ligand-1 (PD-L1) and Programmed Death Ligand-2 (PD-L2), that are expressed on antigen-presenting cells as well as many human cancers and have been shown to downregulate T cell activation and cytokine secretion upon binding to PD-1. Inhibition of the PD-I/PD-LI interaction mediates potent antitumor activity in preclinical models (See, e.g., U.S. Pat. Nos. 8,008,449 and 7,943, 743), and the use of antibody inhibitors of the PD-I/PD-LI interaction for treating cancer has been studied in clinical trials. See, e.g., Topalian S, et al., Targeting the PD-1/B7-H1(PD-L1) pathway to activate antitumor immunity. *Curr Opin Immunol* (2012) 24:207-212; Pardoll D, The blockade of immune checkpoints in cancer immunotherapy. *Nature Reviews Cancer* (2012) 12: 252-264.

Nivolumab (marketed by Bristol-Myers Squibb Company, Princeton, NJ, USA under the tradename "OPDIVO™", also known as 5C4, BMS-936558, MDX-1106, or ONO-4538) is a fully human IgG4 (S228P) PD-1 immune checkpoint inhibitor antibody that selectively prevents interaction with PD-1 ligands (PD-L1 and PD-L2), thereby blocking the down-regulation of antitumor T-cell functions. See, e.g., U.S. Pat. No. 8,008,449; Wang et al. (2014); see also http://www.cancer.gov/drugdictionary?cdrid=695789 (last accessed: Apr. 25, 2017). Pembrolizumab (marketed by Merck & Co., Inc, Whitehouse Station, NJ, USA under the tradename "KEYTRUDA™", also known as lambrolizumab, and MK-3475) is a humanized monoclonal IgG4 antibody directed against human cell surface receptor PD-1. Pembrolizumab is described, for example, in U.S. Pat. Nos. 8,354,509 and 8,900,587; see also http://www.cancer.gov/drugdictionary?cdrid=539833 (last accessed: Apr. 25, 2017).

Ipilimumab (marketed by Bristol-Myers Squibb Company, Princeton, NJ, USA under the tradename "YERVOY™") is a fully human, IgG1 monoclonal antibody that blocks the binding of CTLA-4 to its B7 ligands, thereby stimulating T cell activation and improving overall survival in patients with advanced melanoma. Ipilimumab is described, for example, in U.S. Pat. No. 6,984,720; see also http://www.cancer.gov/drugdictionary?cdrid=38447 (last accessed: Apr. 25, 2017).

Examples of other therapeutic approaches to cancer with immunology targeting anti-cancer agents include other antibodies that target a variety of receptors, as well as peptides, proteins, small molecules, adjuvants, cytokines, oncolytic viruses, vaccines, bi-specific molecules and cellular therapeutic agents. See, e.g., Ott P, et al. Combination immunotherapy: a road map Journal for ImmunoTherapy of Cancer (2017) 5:16 doi: 10.1186/s40425-017-0218-5, and Hoos A, Development of immuno-oncology drugs—from CTLA4 to PD1 to the next generations, *Nat Rev Drug Discov.* 2016 April; 15(4):235-47. doi: 10.1038/nrd.2015.35.

Despite the benefits that patients have received through the treatment of cancer by immunotherapy, improvements are desired. For example, improved responses by patients in areas such as, for example, overall survival, quality of life, overall response rate, duration of response, progression free survival, patient reported outcome, minimal residual disease or immune response are desired.

SUMMARY OF THE INVENTION

The present invention is directed to combination immunotherapy having a glutamate modulating agent and an immunotherapy agent to treat disease, particularly cancer. By virtue of the present invention, it may now be possible to provide more effective immuno-oncology treatments to patients. Patients may experience an improved response in one or more areas including, for example, overall survival, quality of life, overall response rate, duration of response, progression free survival, patient reported outcome, minimal residual disease or immune response.

In one aspect of the invention, there is provided a method of treating cancer in a patient in need thereof, comprising administering to the patient a therapeutically effective amount of a glutamate modulator and an immunotherapeutic anti-cancer agent.

In one aspect, the glutamate modulator is an agent that promotes the modulation, regulation, attenuation or potentiation of: (i) an ionotropic glutamate receptor; (ii) a metabotropic glutamate receptor; or (iii) a glutamate transporter. In one aspect, the glutamate modulator is an agent that inhibits glutamate release. In one aspect, the glutamate modulator is an agent that modulates, regulates, attenuates or potentiates the metabolism of glutamate or glutamine. In one aspect, the ionotropic glutamate receptor is selected from NMDA, AMPA and kainite. In one aspect, the metabotropic glutamate receptor is one or more of: a group 1 receptor selected from mGluR1 and mGluR5; a group II receptor selected from mGluR2 and mGluR3; or a group III receptor selected from mGluR4, mGluR6, mGluR7, and mGluR8. In one aspect, the glutamate transporter is expressed in glia or in neurons.

In one aspect of the invention, the glutamate modulator is selected from riluzole, memantine, n-acetlcysteine, amantadine, topiramate, pregabalin, lamotrigine, ketamine, s-ketamine, AZD8108, AZD 6765 (lanicemine), BHV-4157 (trigriluzole), dextromethorphan, AV-101, CERC-301, GLY-13, and pharmaceutically acceptable salts, prodrugs or analogs thereof.

In one aspect of the invention, the immunotherapeutic anti-cancer agent is selected from antibodies, peptides, proteins, small molecules, adjuvants, cytokines, oncolytic viruses, vaccines, bi-specific molecules and cellular therapeutic agents. In one aspect, the immunotherapeutic anti-cancer agent is a checkpoint inhibitor. In one aspect, the checkpoint inhibitor is an inhibitor of a checkpoint receptor selected from PD-1, PD-L1 and CTLA-4. In one aspect, the inhibitor of PD-1 is an anti-PD-1 antibody selected from nivolumab, pembrolizumab and pidilzumab. In one aspect, the inhibitor of PD-LI is anti-PD-LI antibody selected from BMS-936559, durvalumab, atezolizumab, avelumab, and MDX-1105. In one aspect, the inhibitor of PD-L1 is a peptide. In one aspect, the inhibitor of CTLA-4 is an anti-CTLA-4 antibody selected from ipilimumab and tremelimumab.

In one aspect of the invention, the glutamate modulator and the immunotherapeutic anti-cancer agent are capable of providing a Mouse Survival Ratio of at least 2.0 at day 60 ($MSR_{60}$)

In one aspect of the invention, there is provided a method for modulating glutamate in a patient being treated with an immunotherapeutic anti-cancer agent comprising contacting a glutamate receptor or a glutamate transporter in the patient with a glutamate modulating agent at a time proximate to the treatment with the immunotherapeutic anti-cancer agent. In one aspect, the glutamate modulating agent is riluzole. In one aspect, the riluzole is administered intravenously, intramuscularly, parenterally, sublingually, nasally or orally. In one aspect, the riluzole is administered in the form of a prodrug. In one aspect, the prodrug has the following formula:

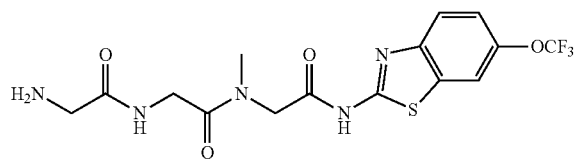 [SMILES: CN(CC(=O)Nc1nc2ccc(OC(F)(F)F)cc2s1)C(=O)CNC(=O)CN]

In one aspect, the contacting of the glutamate receptor or glutamate transporter with the glutamate modulating agent is conducted before, concurrently, or after the treatment with the immunotherapeutic anti-cancer agent. In one aspect, the proximate time is within one (1) week of the treatment with the immunotherapeutic anti-cancer agent.

In one aspect of the invention, there is provided a method of sensitizing a patient afflicted with cancer being treated with an immunotherapeutic anti-cancer agent comprising administering to the patient a therapeutically effective amount of a glutamate modulating agent at a time proximate to the treatment with the immunotherapeutic anti-cancer agent. In one aspect, the sensitization promotes enhanced anti-tumor efficacy. In one aspect, the enhanced anti-tumor efficacy is measured by an increased objective response rate or an increased response duration of the patient.

In one aspect, the enhanced anti-tumor efficacy promotes an increase in the overall survival of the patient. In one aspect, the patient exhibits an overall survival of at least about 10 months, at least about 11 months, at least about 12 months, at least about 13 months, at least about 14 months at least about 15 months, at least about 16 months, at least about 17 months, at least about 18 months, at least about 19 months, at least about 20 months, at least about 21 months, at least about 22 months, at least about 23 months, at least about 2 years, at least about 3 years, at least about 4 years, or at least about 5 years after the initial administration of the immunotherapeutic anti-cancer agent. In one aspect, the overall survival of the is at least about 1.1 times, at least about 1.2 times, at least about 1.3 times, at least about 1.4 times, at least about 1.5 times, at least about 2.0 times, at least about 3.0 times, or at least about 3.0 times the overall survival of a patient treated with a therapeutically effective amount of an immunotherapeutic anti-cancer agent but without a glutamate modulating agent.

In one aspect of the invention, there is provided a method for improving a response in a patient afflicted with cancer being treated with an immunotherapeutic anti-cancer agent comprising administering to the patient in need thereof, an effective amount of the immunotherapeutic anti-cancer agent and riluzole or a prodrug thereof. In one aspect, the immunotherapeutic anti-cancer agent is a checkpoint inhibitor. In one aspect, the checkpoint inhibitor is an inhibitor of a checkpoint receptor selected from PD-1, PD-LI, and CTLA-4. In one aspect, the patient is additionally treated with an antibody selected from an anti-LAG3 antibody, an anti-CD137 antibody, an anti-KIR antibody, an anti-TGFp antibody, an anti-IL-10 antibody, an anti-B7-H4 antibody, an anti-Fas ligand antibody, an anti-CXCR4 antibody, an anti-mesothelin antibody, an anti-CD20 antibody, an anti-CD27 antibody, an anti-GITR antibody, an anti-OX40 antibody, or any combination thereof. In one aspect, the patient is additionally treated with radiation therapy, chemotherapy, a vaccine, a cytokine, a tyrosine kinase inhibitor, an anti-VEGF inhibitor, an IDO inhibitor, an IDO1 inhibitor, a TGF-beta inhibitor, or any combination thereof.

In one aspect of the invention, the cancer is selected from melanoma cancer, renal cancer, prostate cancer, breast cancer, colon cancer, lung cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the CNS, primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and any combinations thereof.

In one aspect, the improved response is one or more of overall survival, quality of life, overall response rate, duration of response, progression free survival, patient reported outcome, minimal residual disease or immune response.

In one aspect of the invention, there is provided a kit for treating a patient afflicted with cancer, the kit comprising:
 (a) an immunotherapeutic anti-cancer a gent; and
 (b) instructions for administering the immunotherapeutic anti-cancer agent in combination with a glutamate modulating agent in the methods of the invention. In one aspect, the immunotherapeutic anti-cancer agent is selected from nivolumab, pembrolizumab, pidilzumab, durvalumab, atezolizumab, avelumab, ipilimumab and tremelimumab.

In one aspect of the invention, there is provided a kit for treating a patient afflicted with cancer, the kit comprising:
 (a) glutamate modulating agent; and
 (b) instructions for administering the glutamate modulating agent in combination with an immunotherapeutic anti-cancer agent in the methods of the invention. In one aspect, the glutamate modulating agent is riluzole or a prodrug thereof These and other aspects and features of the invention will be apparent from the Figure and the Detailed Description.

BRIEF DESCRIPTION OF THE DRAWINGS

These and/or other aspects will become apparent and more readily appreciated from the following description of the embodiments, taken in conjunction with the accompanying drawings that should not be considered limiting in any way, in which:

FIG. 2 illustrates a specific protocol of the study described in Example 1.

DETAILED DESCRIPTION OF THE INVENTION

Figure 1:
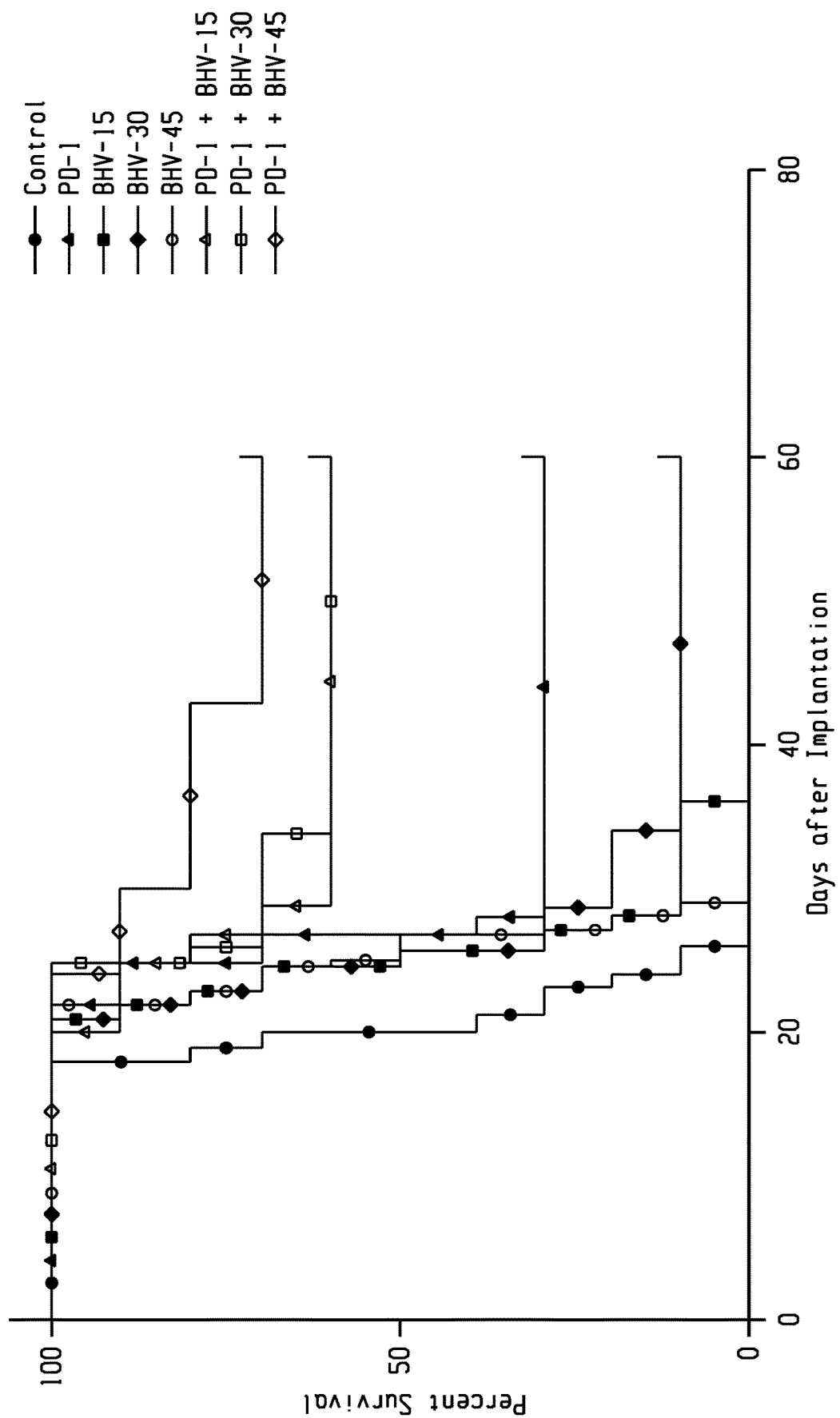
FIG. 1 illustrates the results of the test described in Example 1, showing survival in a glioblastoma animal model testing a riluzole prodrug (BHV-4157), an anti-PD-1 antibody, alone and in combinations along with a control.

The following detailed description is provided to aid those skilled in the art in practicing the present invention. Those of ordinary skill in the art may make modifications and variations in the embodiments described herein without departing from the spirit or scope of the present disclosure. Unless otherwise defined, all technical and scientific terms used herein have the same meaning as commonly understood by one of ordinary skill in the art to which this disclosure belongs. The terminology used in the description is for describing particular embodiments only and is not intended to be limiting.

As used in this application, except as otherwise expressly provided herein, each of the following terms shall have the meaning set forth below. Additional definitions are set forth throughout the application. In instances where a term is not specifically defined herein, that term is given an art-recognized meaning by those of ordinary skill applying that term in context to its use in describing the present invention.

The articles "a" and "an" refer to one or to more than one (i.e., to at least one) of the grammatical object of the article unless the context clearly indicates otherwise. By way of example, "an element" means one element or more than one element.

The term "about" refers to a value or composition that is within an acceptable error range for the particular value or composition as determined by one of ordinary skill in the art, which will depend in part on how the value or composition is measured or determined, i.e., the limitations of the measurement system. For example, "about" can mean within 1 or more than 1 standard deviation per the practice in the art. Alternatively, "about" can mean a range of up to 10% or 20% (i.e., ±10% or ±20%). For example, about 3 mg can include any number between 2.7 mg and 3.3 mg (for 10%) or between 2.4 mg and 3.6 mg (for 20%). Furthermore, particularly with respect to biological systems or processes, the terms can mean up to an order of magnitude or up to 5-fold of a value. When particular values or compositions are provided in the application and claims, unless otherwise stated, the meaning of "about" should be assumed to be within an acceptable error range for that particular value or composition.

The term "ALS" refers to Amyotrophic Lateral Sclerosis.

The term "administering" refers to the physical introduction of a composition comprising a therapeutic agent to a subject, using any of the various methods and delivery systems known to those skilled in the art. For example, routes of administration for immune checkpoint inhibitors, e.g., an anti-PD-1 antibody or an anti-PD-L1 antibody, can include intravenous, intramuscular, subcutaneous, intraperitoneal, spinal or other parenteral routes of administration, for example by injection or infusion. The phrase "parenteral administration" as used herein means modes of administration other than enteral and topical administration, usually by injection, and includes, without limitation, intravenous, intramuscular, intraarterial, intrathecal, intralymphatic, intralesional, intracapsular, intraorbital, intracardiac, intradermal, intraperitoneal, transtracheal, subcutaneous, subcuticular, intraarticular, subcapsular, subarachnoid, intraspinal, epidural and intrasternal injection and infusion, as well as in vivo electroporation. In some embodiments, immunotherapeutic anticancer agents, e.g., immune checkpoint inhibitors, are administered via a non-parenteral route, in some embodiments, orally. Typical routes of administration for glutamate modulators, e.g., riluzole, can include bucal, intranasal, ophthalmic, oral, osmotic, parenteral, rectal, sublingual, topical, transdermal, or vaginal. Administering can also be performed, for example, once, a plurality of times, and/or over one or more extended periods and can be a therapeutically effective dose or a subtherapeutic dose.

The term "anti-antigen" antibody refers, without limitation, to an antibody that binds specifically to the antigen. For example, an anti-PD-1 antibody binds specifically to PD-1 and an anti-CTLA-4 antibody binds specifically to CTLA-4.

The term "antigen-binding portion" of an antibody (also called an "antigen-binding fragment") refers, without limitation, to one or more fragments of an antibody that retain the ability to bind specifically to the antigen bound by the whole antibody.

The term "antibody" (Ab) refers to, without limitation, a glycoprotein immunoglobulin which binds specifically to an antigen and comprises at least two heavy (H) chains and two light (L) chains interconnected by disulfide bonds, or an antigen-binding portion thereof. Each H chain comprises a heavy chain variable region (abbreviated herein as $V_H$) and a heavy chain constant region. The heavy chain constant region comprises three constant domains, $C_{H1}$, $C_{H2}$ and $C_{H3}$. Each light chain comprises a light chain variable region (abbreviated herein as $V_L$) and a light chain constant region. The light chain constant region comprises one constant domain, $C_L$. The $V_H$ and $V_L$ regions can be further subdivided into regions of hypervariability, termed complementarity determining regions (CDRs), interspersed with regions that are more conserved, termed framework regions (FR). Each $V_H$ and $V_L$ comprises three CDRs and four FRs, arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1q) of the classical complement system.

An immunoglobulin can derive from any of the commonly known isotypes, including but not limited to IgA, secretory IgA, IgG and IgM. IgG subclasses are also well known to those in the art and include but are not limited to human IgG1, IgG2, IgG3 and IgG4. "Isotype" refers, without limitation, to the antibody class or subclass (e.g., IgM or IgG1) that is encoded by the heavy chain constant region genes. In certain embodiments, one or more amino acids of the isotype can be mutated to alter effector function. The term "antibody" includes, by way of example, both naturally occurring and non-naturally occurring Abs; monoclonal and polyclonal Abs; chimeric and humanized Abs; human or nonhuman Abs; wholly synthetic Abs; and single chain antibodies. A nonhuman antibody can be humanized by recombinant methods to reduce its immunogenicity in man. Where not expressly stated, and unless the context indicates otherwise, the term "antibody" also includes an antigen-binding fragment or an antigen-binding portion of any of the aforementioned immunoglobulins, and includes a monovalent and a divalent fragment or portion, and a single chain antibody.

The term "AUC" (area under the curve) refers to a total amount of drug absorbed or exposed to a subject. Generally, AUC may be obtained from mathematical method in a plot of drug concentration in the subject over time until the concentration is negligible. The term "AUC" (area under the curve) could also refer to partial AUC at specified time intervals (as may be the case with sublingual absorption which would increase AUC at earlier time intervals).

The term "cancer" refers to a broad group of various diseases characterized by the uncontrolled growth of abnormal cells in the body. Unregulated cell division and growth results in the formation of malignant tumors that invade neighboring tissues and can also metastasize to distant parts of the body through the lymphatic system or bloodstream. "Cancer" includes primary, metastatic and recurrent cancers as well as a precancerous condition, i.e., a state of disordered morphology of cells that is associated with an increased risk of cancer. The term "cancer" includes, but is not limited to, the following proliferative diseases: Acute Lymphoblastic Leukemia (ALL), Acute Myeloid Leukemia (AML), Adrenocortical Carcinoms, Childhood cancers, AIDS-Related Cancers, Kaposi Sarcoma, AIDS-Related Lymphoma, Primary CNS Lymphoma, Anal Cancer, Astrocytomas, Atypical Teratoid/Rhabdoid Tumor, Basal Cell Carcinoma, Skin Cancer (Nonmelanoma), Bile Duct Cancer, Bladder Cancer, Bone Cancer, Ewing Sarcoma Family of Tumors, Osteosarcoma and Malignant Fibrous Histiocytoma, Brain Stem Glioma, Atypical Teratoid/Rhabdoid Tumor, Embryonal Tumors, Germ Cell Tumors, Craniopharyngioma, Ependymoma, Breast Cancer, Bronchial Tumors, Burkitt Lymphoma, Non-Hodgkin Lymphoma, Carcinoid Tumor, Gastrointestinal Carcinoma, Cardiac (Heart) Tumors, Primary Lymphoma, Cervical Cancer, Cholangiocarcinoma, Chordoma, Chronic Lymphocytic Leukemia (CLL), Chronic Myelogenous Leukemia (CML), Chronic Myeloproliferative Neoplasms, Colon Cancer, Colorectal Cancer, Craniopharyngioma, Cutaneous T-Cell Lymphoma, Mycosis Fungoides and Sézary Syndrome, Ductal Carcinoma In Situ (DCIS), Embryonal Tumors, Endometrial Cancer, Ependymoma, Esophageal Cancer, Esthesioneuroblastoma, Extracranial Germ Cell Tumor, Extragonadal Germ Cell Tumor, Eye Cancer, Intraocular Melanoma, Retinoblastoma, Fallopian Tube Cancer, Fibrous Histiocytoma of Bone, Malignant, and Osteosarcoma, Gallbladder Cancer, Gastric (Stomach) Cancer, Gastrointestinal Carcinoid Tumor, Gastrointestinal Stromal Tumors (GIST), Germ Cell Tumor, Ovarian, Testicular, Gestational Trophoblastic Disease, Glioma, Hairy Cell Leukemia, Head and Neck Cancer, Hepatocellular (Liver) Cancer, Histiocytosis, Langerhans Cell, Hodgkin Lymphoma, Hypopharyngeal Cancer, Islet Cell Tumors, Pancreatic Neuroendocrine Tumors, Kaposi Sarcoma, Kidney, Renal Cell, Langerhans Cell Histiocytosis, Laryngeal Cancer, Leukemia, Acute Lymphoblastic (ALL), Acute Myeloid (AML), Chronic Lymphocytic (CLL), Chronic Myelogenous (CML), Hairy Cell, Lip and Oral Cavity Cancer, Liver Cancer (Primary), Lung Cancer, Non-Small Cell, Small Cell, Lymphoma, Hodgkin, Non-Hodgkin, Macroglobulinemia, Waldenström, Male Breast Cancer, Melanoma, Merkel Cell Carcinoma, Mesothelioma, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic (CML), Myeloid Leukemia, Acute (AML) Myeloma, Multiple, Myeloproliferative Neoplasms, Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and Oropharyngeal Cancer, Osteosarcoma and Malignant Fibrous Histiocytoma of Bone, Ovarian Cancer, Low Malignant Potential Tumor, Pancreatic Cancer, Pancreatic Neuroendocrine Tumors (Islet Cell Tumors), Papillomatosis, Paraganglioma, Paranasal Sinus and Nasal Cavity Cancer, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Pregnancy and Breast Cancer, Primary CNS Lymphoma, Primary Peritoneal Cancer, Prostate Cancer, Rectal Cancer, Renal Cell (Kidney) Cancer, Renal Pelvis and Ureter, Transitional Cell Cancer, Retinoblastoma, Rhabdomyosarcoma, Salivary Gland Cancer, Rhabdomyosarcoma, Uterine, Small Intestine Cancer, Soft Tissue Sarcoma, Sqamous Cell Carcinoma, Squamous Neck Cancer with Occult Primary, Metastatic, Stomach (Gastric) Cancer, T-Cell Lymphoma, Testicular Cancer, Throat Cancer, Thymoma and Thymic Carcinoma, Thyroid Cancer, Transitional Cell Cancer of the Renal Pelvis and Ureter, Unknown Primary, Ureter and Renal Pelvis, Transitional Cell Cancer, Urethral Cancer, Uterine Cancer, Endometrial, Uterine Sarcoma, Vaginal Cancer, Vulvar Cancer, Waldenström Macroglobulinemia, and Wilms Tumor.

The term "chimeric antibody" refers, without limitation, to an antibody in which the variable regions are derived from one species and the constant regions are derived from another species, such as an antibody in which the variable regions are derived from a mouse antibody and the constant regions are derived from a human antibody.

The term "Cmax" refers to a maximum concentration of a drug in blood, serum, a specified compartment or test area of a subject between administration of a first dose and administration of a second dose. The term Cmax could also refer to dose normalized ratios if specified.

The term "Cytotoxic T-Lymphocyte Antigen-4" (CTLA-4) refers to an immunoinhibitory receptor belonging to the CD28 family. CTLA-4 is expressed exclusively on T cells in vivo, and binds to two ligands, CD80 and CD86 (also called B7-1 and B7-2, respectively). The term "CTLA-4" includes human CTLA-4 (hCTLA-4), variants, isoforms, and species homologs of hCTLA-4, and analogs having at least one common epitope with hCTLA-4. The complete hCTLA-4 sequence can be found under GenBank Accession No. AAB59385.

The term "dosing interval," refers to the amount of time that elapses between multiple doses of a formulation disclosed herein being administered to a subject. Dosing interval can thus be indicated as ranges.

The term "dosing frequency" refers to the frequency of administering doses of a formulation disclosed herein in a given time. Dosing frequency can be indicated as the number of doses per a given time, e.g., once a week or once in two weeks.

The term "effective amount" refers to that amount which is sufficient to effect an intended result. The effective amount will vary depending on the subject and disease state being treated, the severity of the affliction and the manner of administration, and may be determined routinely by one of ordinary skill in the art.

The term "flat dose" refers to a dose that is administered to a patient without regard for the weight or body surface area (BSA) of the patient. The flat dose is therefore not provided as a mg/kg dose, but rather as an absolute amount of the agent (e.g., the anti-PD-1 antibody). For example, a 60 kg person and a 100 kg person would receive the same dose of the antibody (e.g., 240 mg of an anti-PD-1 antibody).

The term "fixed dose" with regard to a composition of the invention refers to two or more different therapeutic agents in a single composition are present in the composition in particular (fixed) ratios with each other. In some embodiments, the fixed dose is based on the weight (e.g., mg) of the therapeutic agents. In certain embodiments, the fixed dose is based on the concentration (e.g., mg/ml) of two antibodies. In some embodiments, the ratio is at least about 1:1, about 1:2, about 1:3, about 1:4, about 1:5, about 1:6, about 1:7, about 1:8, about 1:9, about 1:10, about 1:15, about 1:20, about 1:30, about 1:40, about 1:50, about 1:60, about 1:70, about 1:80, about 1:90, about 1:100, about 1:120, about 1:140, about 1:160, about 1:180, about 1:200, about 200:1, about 180:1, about 160:1, about 140:1, about 120:1, about 100:1, about 90:1, about 80:1, about 70:1, about 60:1, about 50:1, about 40:1, about 30:1, about 20:1, about 15:1, about 10:1, about 9:1, about 8:1, about 7:1, about 6:1, about 5:1, about 4:1, about 3:1, or about 2:1 mg first antibody to mg second antibody. For example, the 3:1 ratio of a first antibody and a second antibody can mean that a vial can contain about 240 mg of the first antibody and 80 mg of the second antibody or about 3 mg/ml of the first antibody and 1 mg/ml of the second antibody.

The term "human antibody" (HuMAb) refers, without limitation, to an antibody having variable regions in which both the framework and CDR regions are derived from human germline immunoglobulin sequences. Furthermore, if the antibody contains a constant region, the constant region also is derived from human germline immunoglobulin sequences. The human antibodies of the invention can include amino acid residues not encoded by human germline immunoglobulin sequences (e.g., mutations introduced by random or site-specific mutagenesis in vitro or by somatic mutation in vivo). However, the term "human antibody," as used herein, is not intended to include antibodies in which CDR sequences derived from the germline of another mammalian species, such as a mouse, have been grafted onto human framework sequences. The terms "human" antibodies and "fully human" antibodies and are used synonymously.

A "humanized antibody" refers, without limitation, to an antibody in which some, most or all of the amino acids outside the CDR domains of a non-human antibody are replaced with corresponding amino acids derived from human immunoglobulins. In one embodiment of a humanized form of an antibody, some, most or all of the amino acids outside the CDR domains have been replaced with amino acids from human immunoglobulins, whereas some, most or all amino acids within one or more CDR regions are unchanged. Small additions, deletions, insertions, substitutions or modifications of amino acids are permissible as long as they do not abrogate the ability of the antibody to bind to a particular antigen. A "humanized" antibody retains an antigenic specificity similar to that of the original antibody.

The terms "immunotherapeutic anti-cancer agent", "immunotherapy agent", and "immuno-oncology agent" refer to an agent that does not directly attack a tumor but instead mobilize the immune system by adaptive or innate immunity of a subject, and such agents encompass a broad range of agents, including, for example, antibodies, peptides, proteins, small molecules, adjuvants, cytokines, oncolytic viruses, vaccines, bi-specific molecules and cellular therapies. The immunotherapeutic anti-cancer agent includes any agent that targets the immune system to result in an anti-cancer therapeutic effects. Such targets and agents include but are not limited to: anti-PD-1, anti-PD-L1, anti-CTLA4 or other immunotherapy or checkpoint inhibitor targets.

The term "immunotherapy" refers to the treatment of a subject afflicted with, or at risk of contracting or suffering a recurrence of, a disease by a method comprising inducing, enhancing, suppressing or otherwise modifying an immune response.

The term "immune-related" response pattern refers to a clinical response pattern often observed in cancer patients treated with immunotherapeutic agents that produce antitumor effects by inducing cancer-specific immune responses or by modifying native immune processes. This response pattern is characterized by a beneficial therapeutic effect that follows an initial increase in tumor burden or the appearance of new lesions, which in the evaluation of traditional chemotherapeutic agents would be classified as disease progression and would be synonymous with drug failure. Accordingly, proper evaluation of immunotherapeutic agents can require long-term monitoring of the effects of these agents on the target disease.

The terms "in combination with" and "in conjunction with" refer to administration of one treatment modality in addition to another treatment modality. As such, "in combination with" or "in conjunction with" refers to administration of one treatment modality before, during, or after administration of the other treatment modality to the subject.

An "isolated antibody" refers, without limitation, to an antibody that is substantially free of other antibodies having different antigenic specificities (e.g., an isolated antibody that binds specifically to PD-1 is substantially free of antibodies that bind specifically to antigens other than PD-1). An isolated antibody that binds specifically to PD-1 can, however, have cross-reactivity to other antigens, such as PD-1 molecules from different species. Moreover, an isolated antibody can be substantially free of other cellular material and/or chemicals.

The term "monoclonal antibody" ("mAb") refers, without limitation, to a non-naturally occurring preparation of antibody molecules of single molecular composition, i.e., antibody molecules whose primary sequences are essentially identical, and which exhibits a single binding specificity and affinity for a particular epitope. A mAb is an example of an isolated antibody. MAbs can be produced by hybridoma, recombinant, transgenic or other techniques known to those skilled in the art.

The term "Mouse Survival Ratio", also referred to as "$MSR_x$," refers to a value calculated by dividing: (i) the percentage survival of mice treated with an immunotherapeutic anti-cancer agent plus a glutamate modulating agent, by (ii) the percentage survival of mice treated with an immunotherapeutic anti-cancer agent alone, in accordance with the procedure set forth in Example 1 hereof at a time period of "x" number of days after implantation of the tumor into the mice. Thus, $MSR_{60}$ refers to the Mouse Survival Ratio at a time of 60 days after tumor implantation.

The term "pharmaceutically acceptable salt" refers to a salt form of one or more of the compounds or prodrugs described herein which are presented to increase the solubility of the compound in the gastric or gastroenteric juices of the patient's gastrointestinal tract in order to promote dissolution and the bioavailability of the compounds. Pharmaceutically acceptable salts include those derived from pharmaceutically acceptable inorganic or organic bases and acids, where applicable. Suitable salts include those derived from alkali metals such as potassium and sodium, alkaline earth metals such as calcium, magnesium and ammonium salts, among numerous other acids and bases well known in the pharmaceutical art.

Programmed Death-1 (PD-1)" refers to an immunoinhibitory receptor belonging to the CD28 family. PD-1 is expressed predominantly on previously activated T cells in vivo, and binds to two ligands, PD-L1 and PD-L2. The term "PD-1" as used herein includes human PD-1 (hPD-1), variants, isoforms, and species homologs of hPD-1, and analogs having at least one common epitope with hPD-1. The complete hPD-1 sequence can be found under GenBank Accession No. U64863.

Programmed Death Ligand-1 (PD-L1)" is one of two cell surface glycoprotein ligands for PD-1 (the other being PD-L2) that downregulate T cell activation and cytokine secretion upon binding to PD-1. The term "PD-L1" as used herein includes human PD-L1 (hPD-L1), variants, isoforms, and species homologs of hPD-L1, and analogs having at least one common epitope with hPD-L1. The complete hPD-L1 sequence can be found under GenBank Accession No. Q9NZQ7.

The term "prodrug" refers to a precursor of a drug which may be administered in an altered or less active form. The prodrug may be converted into the active drug form in physiological environments by hydrolysis or other metabolic pathways. A discussion of prodrugs is provided in T. Higuchi and V. Stella, Pro-drugs as Novel Delivery Systems (1987) 14 of the *A.C.S. Symposium Series*, and in Bioreversible Carriers in Drug Design, (1987) Edward B. Roche, ed., American Pharmaceutical Association and Pergamon Press.

The term "sublingual administration" refers to a route of administrating a chemical agent or a drug by placing thereof under a tongue of a subject.

The terms "subject" and "patient" refer any human or nonhuman animal. The term "nonhuman animal" includes, but is not limited to, vertebrates such as nonhuman primates, sheep, dogs, and rodents such as mice, rats and guinea pigs. In some embodiments, the subject is a human. The terms, "subject" and "patient" are used interchangeably herein.

The term, "subtherapeutic dose" refers a dose of a therapeutic agent (e.g., an antibody or a glutamate modulator) that is lower than the usual or typical dose of the therapeutic agent when administered alone for the treatment of a disease (e.g., cancer). In some aspects of the invention, a therapeutically effective amount can include a subtherapeutic dose of either the immunotherapeutic anti-cancer agent or the glutamate modulator, or both.

The terms "therapeutically effective amount", "therapeutically effective dosage" and "therapeutically effective dose" of an agent (also sometimes referred to herein as a "drug") refers to any amount of the agent that, when used alone or in combination with another agent, protects a subject against the onset of a disease or promotes disease regression evidenced by a decrease in severity of disease symptoms, an increase in frequency and duration of disease symptom-free periods, or a prevention of impairment or disability due to the disease affliction. The ability of an agent to promote disease regression can be evaluated using a variety of methods known to the skilled practitioner, such as in human subjects during clinical trials, in animal model systems predictive of efficacy in humans, or by assaying the activity of the agent in in vitro assays. In certain embodiments, the therapeutically effective amount prevents the development or recurrence of the cancer entirely. "Inhibiting" the development or recurrence of a cancer means either lessening the likelihood of the cancer's development or recurrence, or preventing the development or recurrence of the cancer entirely.

The term "Tmax" refers to a time or period after administration of a drug when the maximum concentration (Cmax) is reached in blood, serum, a specified compartment or test area of a subject.

The term "treatment" refers to any treatment of a condition or disease in a subject and may include: (i) preventing the disease or condition from occurring in the subject which may be predisposed to the disease but has not yet been diagnosed as having it; (ii) inhibiting the disease or condition, i.e., arresting its development; relieving the disease or condition, i.e., causing regression of the condition; or (iii) ameliorating or relieving the conditions caused by the disease, i.e., symptoms of the disease. Treatment could be used in combination with other standard therapies or alone. Treatment or "therapy" of a subject also includes any type of intervention or process performed on, or the administration of an agent to, the subject with the objective of reversing, alleviating, ameliorating, inhibiting, slowing down or preventing the onset, progression, development, severity or recurrence of a symptom, complication or condition, or biochemical indicia associated with a disease.

The term "weight based dose" refers to a dose that is administered to a patient is calculated based on the weight of the patient. For example, when a patient with 60 kg body weight requires 3 mg/kg of an anti-PD-1 antibody in combination with 1 mg/kg of an anti-CTLA-4 antibody, one can draw the appropriate amounts of the anti-PD-1 antibody (i.e., 180 mg) and the anti-CTLA-4 antibody (i.e., 60 mg) at once from a 3:1 ratio fixed dosing formulation of an anti-PD-1 antibody and an anti-CTLA-4 antibody.

Immune checkpoint inhibitors are preferred for use in accordance with the present invention. Preferred immune checkpoint inhibitors include anti-PD-1 antibodies, anti-PD-L1 antibodies and anti-CTLA-4 antibodies, or any combination thereof that provides the desired efficacy and safety. In some embodiments, the anti-PD-1 antibody, anti-PD-L1 antibody, or antigen-binding portions thereof is a chimeric, humanized or human monoclonal antibody or a portion thereof. In certain embodiments for treating a human subject, the antibody is a humanized antibody. In other embodiments for treating a human subject, the antibody is a human antibody. Antibodies of an IgG1, IgG2, IgG3 or IgG4 isotype can be used.

Preferred immune checkpoint inhibitors suitable for use in accordance with the present invention include anti-PD-1 antibodies that bind to PD-1 with high specificity and affinity, block the binding of PD-L1, and inhibit the immunosuppressive effect of the PD-1 signaling pathway. In any of the therapeutic methods disclosed herein, an anti-PD-1 or anti-PD-L1 antibody includes an antigen-binding portion that binds to the PD-1 or PD-L1 receptor, respectively, and exhibits the functional properties similar to those of whole antibodies in inhibiting ligand binding and upregulating the immune system. In one embodiment, the anti-PD-1 antibody is nivolumab. In one embodiment, the anti-PD-1 antibody is pembrolizumab. In other embodiments, the anti-PD-1 antibody is chosen from the human antibodies 17D8, 2D3, 4H1, 4A11, 7D3 and 5F4 described in U.S. Pat. No. 8,008,449. In still other embodiments, the anti-PD-1 antibody is MEDI0608 (formerly AMP-514), AMP-224, or BGB-A317 or pidilizumab (CT-011).

Anti-PD-1 antibodies usable in accordance with the present invention also include isolated antibodies that bind specifically to human PD-1 and cross-compete for binding to human PD-1 with another antibody, e.g., nivolumab. The ability of antibodies to cross-compete for binding to an antigen indicates that these antibodies bind to the same epitope region of the antigen and sterically hinder the binding of other cross-competing antibodies to that particular epitope region. These cross-competing antibodies are expected to have functional properties very similar those of such an antibody, e.g., nivolumab, by virtue of their binding to the same epitope region of PD-1. Cross-competing antibodies can be readily identified based on their ability to cross-compete with such an antibody, e.g., nivolumab, in standard PD-1 binding assays such as Biacore analysis, ELISA assays or flow cytometry (see, e.g., WO 2013/173223). For administration to human subjects, these cross-competing antibodies can be chimeric antibodies, or humanized or human antibodies. Such chimeric, humanized or human mAbs can be prepared and isolated by methods well known in the art.

Anti-PD-1 antibodies usable in the methods of the present invention also include antigen-binding portions of the above antibodies. The antigen-binding function of an antibody can be performed by fragments of a full-length antibody. Examples of binding fragments encompassed within the term "antigen-binding portion" of an antibody include (i) a Fab fragment, a monovalent fragment consisting of the $V_L$, $V_H$, $C_L$ and $C_{H1}$ domains; (ii) a F(ab")$_2$ fragment, a bivalent fragment comprising two Fab fragments linked by a disulfide bridge at the hinge region; (iii) a Fd fragment consisting of the $V_H$ and $C_{H1}$ domains; and (iv) a Fv fragment consisting of the $V_L$ and $V_H$ domains of a single arm of an antibody.

Antibodies of an IgG1, IgG2, IgG3 or IgG4 isotype can be used in accordance with the present invention. In certain embodiments, the anti-PD-1 antibody or antigen-binding portion thereof comprises a heavy chain constant region which is of a human IgG1 or IgG4 isotype. In certain other embodiments, the sequence of the IgG4 heavy chain constant region of the anti-PD-1 antibody or antigen-binding portion thereof contains an S228P mutation which replaces a serine residue in the hinge region with the proline residue normally found at the corresponding position in IgG1 isotype antibodies. This mutation, which is present in nivolumab, prevents Fab arm exchange with endogenous IgG4 antibodies, while retaining the low affinity for activating Fc receptors associated with wild-type IgG4 antibodies. See, e.g., Wang et al. (2014). In yet other embodiments, the antibody comprises a light chain constant region which is a human kappa or lambda constant region. In other embodiments, the anti-PD-1 antibody or antigen-binding portion thereof is a mAb or an antigen-binding portion thereof.

Anti-PD-1 and anti-PD-L1 target the same signaling pathway and have been shown in clinical trials to exhibit similar levels of efficacy in a variety of cancers, including RCC. See, e.g., Brahmer et al. (2012) N Engl J Med 366:2455-65; Topalian et al. (2012a) N Engl J Med 366: 2443-54; WO 2013/173223). Accordingly, an anti-PD-L1 antibody can be substituted for the anti-PD-1 antibody in any of the therapeutic methods disclosed herein. In certain embodiments, the anti-PD-L1 antibody is BMS-936559 (formerly 12A4 or MDX-1105) (see, e.g., U.S. Pat. No. 7,943,743; WO 2013/173223). In other embodiments, the anti-PD-L1 antibody is MPDL3280A (also known as RG7446). See, e.g., Herbst et al. (2013) J Clin Oncol 31(suppl):3000 and Abstract; U.S. Pat. No. 8,217,149. In other embodiments, the anti-PD-L1 antibody is MED14736. See, e.g., Khleif (2013) In: Proceedings from the European Cancer Congress 2013; Sep. 27-Oct. 1, 2013; Amsterdam, The Netherlands. Abstract 802). In some embodiments, an immune checkpoint inhibitor, e.g., an anti-PD-1 antagonist, used in the present invention is a PD-1 Fc fusion protein.

Preferred immune checkpoint inhibitors suitable for use in accordance with the present invention also include anti-CTLA-4 antibodies. Anti-CTLA-4 antibodies bind to human CTLA-4 so as to disrupt the interaction of CTLA-4 with a human B7 receptor. Since the interaction of CTLA-4 with B7 transduces a signal leading to inactivation of T-cells bearing the CTLA-4 receptor, disruption of the interaction effectively induces, enhances or prolongs the activation of such T cells, thereby inducing, enhancing or prolonging an immune response.

HuMAbs that bind specifically to CTLA-4 with high affinity have been disclosed in U.S. Pat. Nos. 6,984,720 and 7,605,238. Other CTLA-4 mAbs have been described in, for example, U.S. Pat. Nos. 5,977,318, 6,051,227, 6,682,736, and 7,034,121. The CTLA-4 HuMAbs disclosed in U.S. Pat. Nos. 6,984,720 and 7,605,238 have been demonstrated to exhibit one or more of the following characteristics: (a) binds specifically to human CTLA-4 with a binding affinity reflected by an equilibrium association constant ($K_a$) of at least about $10^7 M^{-1}$, or about $10^9 M^{-1}$, or about $10^{10} M^{-1}$ to $10^{11} M^{-1}$ or higher, as determined by Biacore analysis; (b) a kinetic association constant ($k_a$) of at least about $10^3$, about $10^4$, or about $10^5$ $m^{-1}s^{-1}$; (c) a kinetic disassociation constant ($k_d$) of at least about $10^3$, about $10^4$, or about $10^5$ $m^{-1}s^{-1}$; and (d) inhibits the binding of CTLA-4 to B7-1 (CD80) and B7-2 (CD86). Anti-CTLA-4 antibodies preferable for use in the present invention include mAbs that bind specifically to human CTLA-4 and exhibit at least one, at least two or, in one embodiment, at least three of the preceding characteristics. In one embodiment, the anti-CTLA-4 antibody is ipilimumab. Ipilimumab is an anti-CTLA-4 antibody suitable for use in the methods disclosed herein. Ipilimumab is a fully human, IgG1 monoclonal antibody that blocks the binding of CTLA-4 to its B7 ligands, thereby stimulating T cell activation and preferably improving overall survival (OS) in patients with cancer, e.g., advanced melanoma. Another anti-CTLA-4 antibody useful for the present methods is tremelimumab (also known as CP-675,206). Tremelimumab is human IgG2 monoclonal anti-CTLA-4 antibody. Tremelimumab is described, for example, in WO2012/122444, U.S. Publ. No. 2012/263677 and WO2007/113648 A2.

Anti-CTLA-4 antibodies usable in the disclosed methods of the present invention also include isolated antibodies that bind specifically to human CTLA-4 and cross-compete for binding to human CTLA-4 with ipilimumab or tremelimumab or bind to the same epitope region of human CTLA-4 as ipilimumab or tremelimumab. In certain embodiments, the antibodies that cross-compete for binding to human CTLA-4 with, or bind to the same epitope region of human CTLA-4 as does ipilimumab or tremelimumab, are antibodies comprising a heavy chain of the human IgG1 isotype. For administration to human subjects, these cross-competing antibodies are chimeric antibodies, or humanized or human antibodies. Usable anti-CTLA-4 antibodies also include antigen-binding portions of the above antibodies such as Fab, F(ab")$_2$, Fd or Fv fragments.

Lymphocyte Activation Gene-3 (LAG-3) inhibitors may also be suitable for use in accordance with the present invention. LAG-3 includes human LAG-3 (hLAG-3), variants, isoforms, and species homologs of hLAG-3, and analogs having at least one common epitope with hLAG-3. The term "human LAG-3" refers to human sequence LAG-3, such as the complete amino acid sequence of human LAG-3 having Genbank Accession No. NP 002277. The term "mouse LAG-3" refers to mouse sequence LAG-3, such as the complete amino acid sequence of mouse LAG-3 having Genbank Accession No. NP_032505. LAG-3 is also known in the art as, for example, CD223. The human LAG-3 sequence may differ from human LAG-3 of Genbank Accession No. NP_002277 by having, e.g., conserved mutations or mutations in non-conserved regions and the LAG-3 has substantially the same biological function as the human LAG-3 of Genbank Accession No. NP_002277. For example, a biological function of human LAG-3 is having an epitope in the extracellular domain of LAG-3 that is specifically bound by an antibody of the instant disclosure or a biological function of human LAG-3 is binding to MHC Class II molecules. Antibodies that bind to LAG-3 have been disclosed, for example, in WO2015/042246 and U.S. Publ. Nos. 2014/0093511 and 2011/0150892. An exemplary LAG-3 antibody that may be useful for the present invention is 25F7 (described in U.S. Publ. No. 2011/0150892). An additional exemplary LAG-3 antibody that may be useful for the present invention is BMS-986016. In one embodiment, an anti-LAG-3 antibody that may be useful for the present invention cross-competes with 25F7 or BMS-986016. In another embodiment, an anti-LAG-3 antibody that may be useful for the present invention binds to the same epitope as 25F7 or BMS-986016. In other embodiments, an anti-LAG-3 antibody comprises six CDRs of 25F7 or BMS-986016.

Agents that target Anti-CD 137 may be suitable for use in accordance with the present invention. Anti-CD 137 antibodies specifically bind to and activate CD137-expressing immune cells, stimulating an immune response, in particular a cytotoxic T cell response, against tumor cells. Antibodies that bind to CD137 have been disclosed in U.S. Publ. No. 2005/0095244 and U.S. Pat. Nos. 7,288,638, 6,887,673, 7,214,493, 6,303,121, 6,569,997, 6,905,685, 6,355,476, 6,362,325, 6,974,863, and 6,210,669. In some embodiments, the anti-CD137 antibody is urelumab (BMS-663513), described in U.S. Pat. No. 7,288,638 (20H4.9-IgG4 [10C7 or BMS-663513]). In some embodiments, the anti-CD137 antibody is BMS-663031 (20H4.9-IgGI), described in U.S. Pat. No. 7,288,638. In some embodiments, the anti-CD137 antibody is 4E9 or BMS-554271, described in U.S. Pat. No. 6,887,673. In some embodiments, the anti-CD137 antibody is an antibody disclosed in U.S. Pat. Nos. 7,214,493; 6,303, 121; 6,569,997; 6,905,685; or 6,355,476. In some embodiments, the anti-CD137 antibody is 1D8 or BMS-469492; 3H3 or BMS-469497; or 3E1, described in U.S. Pat. No. 6,362,325. In some embodiments, the anti-CD137 antibody is an antibody disclosed in issued U.S. Pat. No. 6,974,863 (such as 53A2). In some embodiments, the anti-CD137 antibody is an antibody disclosed in issued U.S. Pat. No. 6,210,669 (such as 1D8, 3B8, or 3E1). In some embodiments, the antibody is Pfizer's PF-05082566 (PF-2566). In other embodiments, an anti-CD 137 antibody useful for the invention cross-competes with the anti-CD 137 antibodies disclosed herein. In some embodiments, an anti-CD137 antibody binds to the same epitope as the anti-CD137 antibody disclosed herein.

Agents that target KIR may be suitable for use in accordance with the present invention. The terms "Killer Ig-like Receptor", "Killer Inhibitory Receptor", or "KIR", refer to a protein or polypeptide encoded by a gene that is a member of the KIR gene family or by a cDNA prepared from such a gene. A detailed review of the KIR gene family, including the nomenclature of KIR genes and KIR gene products, and Genbank accession numbers for exemplary KIRs, is "The KIR Gene Cluster" by M. Carrington and P. Norman, available at the NCBI web-site called Bookshelf (accessible at ncbi.nlm.nih.gov/books). The term KIR includes human KIR (hKIR), variants, isoforms, and species homologs of hKIR, and analogs having at least one common epitope with hKIR. The sequences of human KIR genes and cDNAs, as well as their protein products, are available in public databases, including GenBank. Non-limiting exemplary GenBank entries of human KIRs have the following accession numbers: KIR2DL1: Genbank accession number U24076, NM_014218, AAR16197, or L41267; KIR2DL2: Genbank accession number U24075 or L76669; KIR2DL3: Genbank accession number U24074 or L41268; KIR2DL4: Genbank accession number X97229; KIR2DS 1: Genbank accession number X89892; KIR2DS2: Genbank accession number L76667; KIR2DS3: Genbank accession number NM O 12312 or L76670 (splice variant); KIR3DL1: Genbank accession number L41269; and KIR2DS4: Genbank accession number AAR26325. A KIR may comprise from 1 to 3 extracellular domains, and may have a long (i.e., more than 40 amino acids) or short (i.e., less than 40 amino acids) cytoplasmic tail. KIR is further described in Intl Publ. No. WO2014/055648. Examples of anti-KIR antibodies have been disclosed in WO2014/055648, WO2005/003168, WO2005/009465, WO2006/072625, WO2006/072626, WO2007/042573, WO2008/084106, WO2010/065939, WO2012/071411 and WO2012/160448. One anti-KIR antibody that may be useful for the present invention is lirilumab (also referred to as BMS-986015, IPH2102, or the S241P variant of 1-7F9), disclosed in WO2008/084106. An additional anti-KIR antibody that may be useful for the present invention is 1-7F9 (also referred to as IPH2101), described in WO2006/003179.

Agents that target GITR may be suitable for use in accordance with the present invention. The terms "GITR", "tumor necrosis factor receptor superfamily member 18", "activation-inducible TNFR family receptor" and "glucocorticoid-induced T FR-related protein" all refer to a protein that is a member of the tumor necrosis factor receptor super family. GITR is encoded for by the TNFRSF18 gene in humans. It is a 241 amino acid type I transmembrane protein characterized by three cysteine pseudo-repeats in the extracellular domain and specifically protects T-cell receptor-induced apoptosis, although it does not protect cells from other apoptotic signals, including Fas triggering, dexamethasone treatment, or UV irradiation. See, e.g, Nocentini, G, et al. (1997) *Proc. Natl. Acad. Sci*, USA 94:6216-622). The term GITR includes human GITR (hGITR), variants, isoforms, and species homologs of hGITR, and analogs having at least one common epitope with hGITR. Three isoforms of hGITR have been identified, all of which share the same extracellular domain, except for its C-terminal portion. Variant 1 (Accession No. NP_004186) consists of 241 amino acids and represents the longest transcript. It contains an extra coding segment that leads to a frame shift, compared to variant 2. The resulting protein (isoform 1) contains a distinct and shorter C-terminus, as compared to isoform 2. Variant 2 (Accession No. NP 683699) encodes the longest protein (isoform 2), consisting of 255 amino acids, and is soluble. Variant 3 (Accession No. NP 683700) contains an extra coding segment that leads to a frame shift, compared to variant 2. The resulting protein (isoform 3) contains a distinct and shorter C-terminus, as compared to isoform 2, and consists of 234 amino acids. GITR activation increases the proliferation and function of effector T cells, as well as abrogating the suppression induced by activated T regulatory cells. In addition, GITR stimulation promotes anti-tumor immunity by increasing the activity of other immune cells such as NK cells, antigen presenting cells, and B cells. Examples of anti-GITR antibodies have been disclosed in WO2015/031667, WO2015/184,099, WO2015/026,684, WO2006/105021, U.S. Pat. Nos. 7,812,135 and 8,388,967 and U.S. Publ. Nos. 2009/0136494, 2014/0220002, 2013/0183321 and 2014/0348841. In one embodiment, an anti-GITR antibody that may be useful for the present invention is TRX518 (described in, for example, Schaer et a/. *Curr Opin Immunol*. (2012) April; 24(2): 217-224, and WO2006/105021). In another embodiment, an anti-GITR antibody that may be useful for the present invention is MK4166 or MK1248 and antibodies described in WO2011/028683 and in U.S. Pat. No. 8,709,424, and comprising, e.g., a VH chain comprising SEQ ID NO: 104 and a VL chain comprising SEQ ID NO: 105, wherein the SEQ ID NOs are from WO2011/028683 or U.S. Pat. No. 8,709,424). In certain embodiments, an anti-GITR antibody is an anti-GITR antibody that is disclosed in WO2015/031667, e.g., an antibody comprising VH CDRs 1-3 comprising SEQ ID NOs: 31, 71 and 63 of WO2015/031667, respectively, and VL CDRs 1-3 comprising SEQ ID NOs: 5, 14 and 30 of WO2015/031667. In certain embodiments, an anti-GITR antibody is an anti-GITR antibody that is disclosed in WO2015/184099, e.g., antibody Hum23 \#\ or Hum231#2, or the CDRs thereof, or a derivative thereof (e.g., pabl967, pabl975 or pabl979). In certain embodiments, an anti-GITR antibody is an anti-GITR antibody that is disclosed in JP2008278814, WO09/009116, WO2013/039954, US20140072566, US20140072565, US20140065152, or WO2015/026684, or is INBRX-110 (INHIBRx), LKZ-145 (Novartis), or MEDI-1873 (MedImmune). In certain embodiments, an anti-GITR antibody is an anti-GITR antibody that is described in PCT/US2015/033991 (e.g., an antibody comprising the variable regions of 28F3, 18E10 or 19D3).

While not intending to provide an exhaustive list of all immuno-oncology agents that may be suitable for use in accordance with the present invention, the following lists a number of agents that are commercially available or in development. Examples of PD-1 antibodies that may be suitable for use in accordance with the present invention include, for example, pembrolizumab, nivolumab, AMP-224, MEDI0680, AMP-514 and REGN2810. Examples of PD-L1 antibodies that may be suitable for use in accordance with the present invention include, for example, atezolizumab, MDX-1105, aurvalumab, avelumab. Examples of CTLA-4 antibodies that may be suitable for use in accordance with the present invention include, for example, ipilimumab and tremelimumab. Examples of KIR antibodies that may be suitable for use in accordance with the present invention include, for example, lirilumab and NNC0141-0000-0100. Examples of LAG3 antibodies that may be suitable for use in accordance with the present invention include, for example, BMS-986016, IMP321 and MK-4280. Examples of GITR antibodies that may be suitable for use in accordance with the present invention include, for example, TRX518, MK-4166 and MK-1248. Examples of OX40 antibodies that may be suitable for use in accordance with the present invention include, for example, MEDI6383, MEDI6469 and MOXR0916. Examples of IDO/IDO1 agents that may be suitable for use in accordance with the present invention include, for example, indoximod, INCB024360, F001287 and NGL919. Examples of TGF-beta agents that may be suitable for use in accordance with the present invention include, for example, sotaracept, fresolimumab, trabedersen, lucanix, LY2157299, and ACE-536. Examples of CD137 antibodies that may be suitable for use in accordance with the present invention include, for example, urelumab and utomilumab. An example of a CD289/TLT9 agent that may be suitable for use in accordance with the present invention is MGN1703. Examples of MUC-1/CD227 agents that may be suitable for use in accordance with the present invention include, for example, ONT-10 and ASN-004. An example of a CCF2 agent that may be suitable for use in accordance with the present invention is PF-04136309. Examples of CD27 antibodies that may be suitable for use in accordance with the present invention include, for example, varlilumab and AMG172. An example of a CD40 antibody that may be suitable for use in accordance with the present invention is dacetuzumab. An example of a SLAMF7/CS1 antibody that may be suitable for use in accordance with the present invention is elotuzumab. An example of a CD20 agent that may be suitable for use in accordance with the present invention is DI-Leu16-IL2. An example of a CD70 agent that may be suitable for use in accordance with the present invention is ARGX-110. Examples of IL-10 agents that may be suitable for use in accordance with the present invention include, for example, AM0010 and MK-1966. An example of a PSA agent that may be suitable for use in accordance with the present invention is prostvac. An example of a GP100 antibody that may be suitable for use in accordance with the present invention is MDX-1379. An example of a STAT3 agent that may be suitable for use in accordance with the present invention is AZD9150. Examples of IL-12 agents that may be suitable for use in accordance with the present invention include, for example, veledimex, INXN-2001, MSB0010360N, immunopulse, Gen-1 and INO-9012. Examples of IL-2 agents that may be suitable for use in accordance with the present invention include, for example, MSB0010445 and RG7813/RO6895882. An example of a IL-33 agent that may be suitable for use in accordance with the present invention is alarmin IL-33. An example of a M-CSF agent that may be suitable for use in accordance with the present invention is PD-0360324. An example of a hTERT agent that may be suitable for use in accordance with the present invention is INO-1400. An example of a SMAC-mimetic agent that may be suitable for use in accordance with the present invention is birinapant. An example of a ImmTACs agent that may be suitable for use in accordance with the present invention is IMCgp100. An example of a CD-40 agent that may be suitable for use in accordance with the present invention is RO7009789. An example of a CD39 agent that may be suitable for use in accordance with the present invention is IPH52. An example of a CEACAM1 agent that may be suitable for use in accordance with the present invention is MK-6018.

Agents that target VEGF may be suitable for use in accordance with the present invention. Vascular endothelial growth factor ("VEGF") is an endothelial cell-specific mitogen and an inducer of angiogenesis. VEGF has a prominent role in angiogenesis and tumor growth and development. In certain embodiments, the anti-VEGF antagonist is an anti-VEGF antibody, antigen binding molecule or fragment thereof. In certain embodiments, the anti-VEGF antibody is bevacizumab (described in U.S. Pat. No. 7,169,901), or any other VEGF antibody known in the art including ranibizumab (U.S. Pat. No. 7,297,334), VGX-100 (U.S. Pat. No. 7,423,125), r84 (U.S. Pat. No. 8,034,905), aflibercept (U.S. Pat. No. 5,952,199), IMC-18F1 (U.S. Pat. No. 7,972,596), IMC-1C11 (PCT/US2000/02180), and ramucirumab (U.S. Pat. No. 7,498,414).

Agents that target ALK may be suitable for use in accordance with the present invention. ALK inhibitors act on tumours with variations of anaplastic lymphoma kinase (ALK) such as an EML4-ALK translocation. ALK inhibitors that may be useful in accordance with the present invention include crizotinib (Pfizer; Xalkori™, PF-02341066), with the structure described in WHO Drug Information, Vol. 25, No. 1, page 54 (2011); ceritinib (Novartis; Zykadia™, LDK378), with the structure described in WHO Drug Information, Vol. 28, No. 1, page 79 (2014); and alectinib (Roche/Chugai; Alecensa™, RO542802, CH542802), with the structure described in WHO Drug Information, Vol. 27, No. 3, page 70 (2013). Additional examples of ALK inhibitors include, for example, PF-06463922 (Pfizer), NVP-TAE684 (Novartis), AP261 13 (Ariad), TSR-01 1 (Tesaro), X-396 (Xcovery), CEP-37440 (Cephalon/Teva) and RXDX-101 (Igynta; NMS-E628, Nerviano). See, e.g., Wang et al., *Med. Chem. Commun.* 2014, 5:1266. Crizotinib is an inhibitor of anaplastic lymphoma kinase (ALK) and its oncogenic variants (i.e., ALK fusion events and selected oncogenic ALK mutations), as well as the hepatocyte growth factor receptor (HGFR, c-Met), c-ros oncogene 1 (ROS1) and its oncogenic variants, Recepteur d'Origine Nantais (RON) receptor tyrosine kinases (RTKs), LTK, Trk (TrkA, TrkB, TrkC), and/or insulin receptor. XALKORI™ (crizotinib) has been approved in the United States for the treatment of patients with metastatic non-small cell lung cancer (NSCLC) whose tumors are anaplastic lymphoma kinase (ALK)-positive as detected by an FDA-approved test, and has also been approved for the treatment of ALK-positive NSCLC in Europe, Japan and other jurisdictions. Crizotinib, as well as pharmaceutically acceptable salts thereof, is described in WO2006/021884, WO2006/021881 and WO2007/066185, and in U.S. Pat. Nos. 7,858,643, 8,217, 057 and 8,785,632. The use of crizotinib in treating abnormal cell growth, such as cancers, mediated by ALK or c-MET/HGFR is described in WO2007/06617 and U.S. Pat. No. 7,825,137. The use of crizotinib in treating ROS mediated cancers is described in WO2013/017989.

Other antibodies may be suitable for use in accordance with the present invention. In some embodiments, the is an anti-TGFp antibody, as disclosed in WO2009/073533. In some embodiments, the antibody is an anti-IL-10 antibody, as disclosed in WO2009/073533. In some other embodiments, the antibody is an anti-B7-H4 antibody, as disclosed in WO2009/073533. In certain embodiments, the antibody is an anti-Fas ligand antibody, as disclosed in WO2009/073533. In some embodiments, the antibody is an anti-CXCR4 antibody, as disclosed in U.S. Publ. No. 2014/0322208 (e.g., Ulocuplumab (BMS-936564)). In some embodiments the antibody is an anti-mesothelin antibody, as disclosed in U.S. Pat. No. 8,399,623. In some embodiments, the antibody is an anti-HER2 antibody, for example, Herceptin (U.S. Pat. No. 5,821,337), trastuzumab, or ado-trastuzumab emtansine (Kadcyla, e.g., WO2001/000244). In embodiments, the antibody is an anti-CD27 antibody. In embodiments, the anti-CD-27 antibody is Varlilumab (also known as "CDX-1127" and "1F5"), which is a human IgGI antibody that is an agonist for human CD27, as disclosed in, for example, U.S. Pat. No. 9,169,325. In some embodiments, the antibody is an anti-CD73 antibody. In certain embodiments, the anti-CD73 antibody is CD73.4.IgG2C2195.IgGI.

In addition to the antibodies described above, other the immunotherapeutic anti-cancer agents suitable for use in accordance with the present invention include those that function from modalities including peptides, proteins, small molecules, adjuvants, cytokines, oncolytic viruses, vaccines, bi-specific molecules and cellular therapeutic agents.

In accordance with the present invention, additional oncology therapies and agents may be employed including, for example, surgery, radiation, treatment with other agents, antibodies and chemotherapy.

In some embodiments, the immunotherapeutic agent is administered in combination with any chemotherapy known in the art. In certain embodiments, the chemotherapy is a platinum based-chemotherapy. Platinum-based chemotherapies are coordination complexes of platinum. In some embodiments, the platinum-based chemotherapy is a platinum-doublet chemotherapy. In one embodiment, the chemotherapy is administered at the approved dose for the particular indication. In some embodiments, the platinum-based chemotherapy is cisplatin, carboplatin, oxaliplatin, satraplatin, picoplatin, Nedaplatin, Triplatin, Lipoplatin, or combinations thereof. In certain embodiments, the platinum-based chemotherapy is any other platinum-based chemotherapy known in the art. In some embodiments, the chemotherapy is the nucleotide analog gemcitabine. In an embodiment, the chemotherapy is a folate antimetabolite. In an embodiment, the folate antimetabolite is pemetrexed. In certain embodiments the chemotherapy is a taxane. In other embodiments, the taxane is paclitaxel. In other embodiments, the chemotherapy is a nucleoside analog. In one embodiment, the nucleoside analog is gemcitabine. In some embodiments, the chemotherapy is any other chemotherapy known in the art.

In certain embodiments, the immunotherapeutic agent is administered in combination with a tyrosine kinase inhibitor.

In certain embodiments, the tyrosine kinase inhibitor is gefitinib, erlotinib, combinations thereof or any other tyrosine kinase inhibitor known in the art. In some embodiments, the tyrosine kinase inhibitor act on the epidermal growth factor receptor (EGFR). In certain embodiments, the immunotherapeutic agent is administered in combination with a Bruton's tyrosine kinase (Btk) inhibitor. Btk inhibitors useful in treating cancers include those taught in U.S. Pat. No. 8,940,725 (Yamamoto et al.) and U.S. Pat. No. 7,514,444 (Honigberg et al.), U.S. 2015/0118222 (Levy et al.) and WO2017/059224.

Standard-of-care therapies for different types of cancer are well known by persons of skill in the art. For example, the National Comprehensive Cancer Network (NCCN), an alliance of 21 major cancer centers in the USA, publishes the NCCN Clinical Practice Guidelines in Oncology (NCCN GUIDELINES™) that provide detailed up-to-date information on the standard-of-care treatments for a wide variety of cancers (see NCCN GUIDELINES, 2014).

By way of example for the treatment of tumors, a therapeutically effective amount of an immunotherareutic agent can inhibit cell growth or tumor growth by at least about 10%, at least about 20%, by at least about 40%, by at least about 60%, or by at least about 80% relative to untreated subjects or, in certain embodiments, relative to patients treated with a standard-of-care therapy. In other embodiments of the invention, tumor regression can be observed and continue for a period of at least about 20 days, at least about 40 days, or at least about 60 days. Notwithstanding these ultimate measurements of therapeutic effectiveness, evaluation of immunotherapeutic drugs must also make allowance for "immune-related" response patterns.

This present invention provides methods of treating cancer using one or more immunotherapeutic anti-cancer agent, e.g., an anti PD-1 antibody, as monotherapies or in combination with other anti-cancer agents and a glutamate modulating agent. In one embodiment, the cancer is a solid tumor. In another embodiment, the cancer is a primary cancer. In other embodiments, the cancer is a metastatic or recurrent cancer. In some embodiments, the subject is a human patient. In certain embodiments, the subject is a chemotherapy-naïve patient (e.g., a patient who has not previously received any chemotherapy). In other embodiments, the subject has received another cancer therapy (e.g., a chemotherapy), but is resistant or refractory to such another cancer therapy.

Dosage regimens are adjusted to provide the optimum desired response, e.g., a maximal therapeutic response and/or minimal adverse effects. In certain embodiments, the method of the present invention can be used with a flat dose or a weight-based dose. In further embodiments, the immunotherapeutic agent is administered as a flat dose. In further embodiments, the immunotherapeutic agent is administered as a weight-based dose. For administration of an anti-PD-1 antibody, as a monotherapy or in combination with another anti-cancer agent, the dosage can range from about 0.01 to about 20 mg/kg, about 0.1 to about 10 mg/kg, about 0.1 to about 5 mg/kg, about 1 to about 5 mg/kg, about 2 to about 5 mg/kg, about 7.5 to about 12.5 mg/kg, or about 0.1 to about 30 mg/kg of the subject's body weight or from about 80 mg to at least 800 mg, about 80 mg to at about 700 mg, about 80 mg to at about 600 mg, about 80 mg to at about 500 mg, about 80 mg to at about 400 mg, about 80 mg to at about 300 mg, about 100 mg to at about 300 mg, or about 200 mg to about 300 mg. For example, dosages can be about 0.1, about 0.3, about 1, about 2, about 3, about 5 or about 10 mg/kg body weight, or about 0.3, about 1, about 2, about 3, or about 5 mg/kg body weight; or about 80 mg, about 100 mg, about 160 mg, about 200 mg, about 240 mg, about 300 mg, about 320 mg, about 400 mg, about 500 mg, about 600 mg, about 700 mg, or about 800 mg. The dosing schedule is typically designed to achieve exposures that result in sustained receptor occupancy (RO) based on typical pharmacokinetic properties of an antibody. An exemplary treatment regime entails administration about once per week, once about every 2 weeks, once about every 3 weeks, once about every 4 weeks, once about a month, once about every 3-6 months or longer. In certain embodiments, an anti-PD-1 antibody such as nivolumab is administered to the subject once about every 2 weeks. In other embodiments, the antibody is administered once about every 3 weeks. The dosage and scheduling can change during a course of treatment. For example, a dosing schedule for anti-PD-1 monotherapy can comprise administering the Ab: (i) about every 2 weeks in about 6-week cycles; (ii) about every 4 weeks for about six dosages, then about every three months; (iii) about every 3 weeks; (iv) about 3-about 10 mg/kg once followed by about 1 mg/kg every about 2-3 weeks. Considering that an IgG4 antibody typically has a half-life of 2-3 weeks, a dosage regimen for an anti-PD-1 antibody of the invention comprises at least about 0.3 to at least about 10 mg/kg body weight, at least about 1 to at least about 5 mg/kg body weight, or at least about 1 to at least about 3 mg/kg body weight or at least about 80 to at least about 800 mg via intravenous administration, with the antibody being given every about 14-21 days in up to about 6-week or about 12-week cycles until complete response or confirmed progressive disease. In certain embodiments, an anti-PD-1 monotherapy is administered at 3 mg/kg every 2 weeks until progressive disease weeks until progressive disease or unacceptable toxicity. In some embodiments, the antibody treatment, or any combination treatment disclosed herein, is continued for at least about 1 month, at least about 3 months, at least about 6 months, at least about 9 months, at least about 1 year, at least about 18 months, at least about 24 months, at least about 3 years, at least about 5 years, or at least about 10 years. Other examples of dosages for the immunotherapeutic anticancer agent may be about 1-100 mg/kg; for example, 1 mg/kg, 2 mg, kg, 5 mg/kg, 7.5 mg/kg, 10 mg/kg, 20 mg/kg, 25 mg/kg, 50 mg/kg, 75 mg/kg, 100 mg/kg, or any intermediate values.

When used in combinations with other cancer agents, the dosage of an immunotherapeutic agent can be lowered compared to the monotherapy dose. For example, dosages of nivolumab that are lower than the typical 3 mg/kg, but not less than 0.001 mg/kg, are subtherapeutic dosages. The subtherapeutic doses of an anti-PD-1 antibody used in the methods herein are higher than 0.001 mg/kg and lower than 3 mg/kg. In some embodiments, a subtherapeutic dose is about 0.001 mg/kg-about 1 mg/kg, about 0.01 mg/kg-about 1 mg/kg, about 0.1 mg/kg-about 1 mg/kg, or about 0.001 mg/kg-about 0.1 mg/kg body weight. In some embodiments, the subtherapeutic dose is at least about 0.001 mg/kg, at least about 0.005 mg/kg, at least about 0.01 mg/kg, at least about 0.05 mg/kg, at least about 0.1 mg/kg, at least about 0.5 mg/kg, or at least about 1.0 mg/kg body weight. In some embodiments, a subtherapeutic flat does is less than about 240 mg every 2 weeks, for instance about 160 mg or about 80 mg every two weeks. Receptor-occupancy data from 15 subjects who received 0.3 mg/kg to 10 mg/kg dosing with nivolumab indicate that PD-1 occupancy appears to be dose-independent in this dose range. Across all doses, the mean occupancy rate was 85% (range, 70% to 97%), with a mean plateau occupancy of 72% (range, 59% to 81%)

(Brahmer et al. (2010) *J Clin Oncol* 28:3167-75). In some embodiments, 0.3 mg/kg dosing can allow for sufficient exposure to lead to maximal biologic activity In certain embodiments, the dose of an immunotherapeutic agent is a fixed dose in a pharmaceutical composition. In other embodiments, the method of the present invention can be used with a flat dose (a dose given to a patient irrespective of the body weight of the patient). For example, a flat dose of a nivolumab can be about 240 mg. For example, a flat dose of pembrolizumab can be about 200 mg. In some embodiments, the anti-PD-1 antibody or antigen-binding portion thereof is administered at a dose of about 240 mg. In some embodiments, the anti-PD-1 antibody or antigen-binding portion thereof is administered at a dose of about 360 mg. In embodiments, the anti-PD-1 antibody or antigen-binding portion thereof is administered at a dose of about 480 mg. In one embodiment, 360 mg of the anti-PD-1 antibody or antigen binding fragment is administered once every 3 weeks. In another embodiment, 480 mg of the anti-PD-1 antibody or antigen binding fragment is administered once every 4 weeks.

Ipilimumab (YERVOY™) is approved for the treatment of melanoma at 3 mg/kg given intravenously once every 3 weeks for 4 doses. In certain embodiments, the dose of the anti-CTLA-4 antibody is a flat dose, which is given to a patient irrespective of the body weight. In a specific embodiment, the flat dose of the anti-CTLA-4 antibody is about 80 mg.

Thus, in some embodiments, about 3 mg/kg is the highest dosage of ipilimumab used in combination with the anti-PD-1 antibody though, in certain embodiments, an anti-CTLA-4 antibody such as ipilimumab can be dosed within the range of about 0.3 to about 10 mg/kg, about 0.5 to about 10 mg/kg, about 0.5 to about 5 mg/kg, or about 1 to about 5 mg/kg body weight about every two or three weeks when combined with an anti-PD-1 antibody, e.g., nivolumab. In other embodiments, ipilimumab is administered on a different dosage schedule from the anti-PD-1 antibody. In some embodiments, ipilimumab is administered about every week, about every two weeks, about every three weeks, about every four weeks, about every five weeks, about every six weeks, about every seven weeks, about every eight weeks, about every nine weeks, about every ten weeks, about every eleven weeks, about every twelve weeks or about every fifteen weeks.

Dosages of ipilimumab that are lower than the typical 3 mg/kg every 3 weeks, but not less than 0.001 mg/kg, are subtherapeutic dosages. The subtherapeutic doses of an anti-CTLA-4 antibody used in the methods herein are higher than 0.001 mg/kg and lower than 3 mg/kg. In some embodiments, a subtherapeutic dose is about 0.001 mg/kg-about 1 mg/kg, about 0.01 mg/kg-about 1 mg/kg, about 0.1 mg/kg-about 1 mg/kg, or about 0.001 mg/kg-about 0.1 mg/kg body weight. In some embodiments, the subtherapeutic dose is at least about 0.001 mg/kg, at least about 0.005 mg/kg, at least about 0.01 mg/kg, at least about 0.05 mg/kg, at least about 0.1 mg/kg, at least about 0.5 mg/kg, or at least about 1.0 mg/kg body weight. In certain embodiments, the combination of an anti-PD-1 antibody or anti-PD-L1 antibody and an anti-CTLA-4 antibody is administered intravenously to the subject in an induction phase about every 2 or 3 weeks for 1, 2, 3 or 4 administrations. In certain embodiments, the combination of an anti-PD-1 antibody and an anti-PD-L1 antibody is administered intravenously in the induction phase about every 2 weeks or about every 3 weeks for about 4 administrations. The induction phase is followed by a maintenance phase during which only the anti-PD-1 antibody or anti-PD-L1 antibody is administered to the subject at a dosage of about 0.1, about 0.3, about 1, about 2, about 3, about 5 or about 10 mg/kg or about 40 mg, about 80 mg, about 100 mg, about 160 mg, about 200 mg, about 240 mg, about 320 mg or about 400 mg about every two or three weeks for as long as the treatment proves efficacious or until unmanageable toxicity or disease progression occurs. In certain embodiments, nivolumab is administered during the maintenance phase at a dose of about 3 mg/kg body weight or about 240 mg about every 2 weeks.

In certain embodiments, the dose of an anti-PD-1 antibody or an anti-PD-L1 antibody is a fixed dose in a pharmaceutical composition with a second anti-cancer agent. In certain embodiments, the anti-PD-1 antibody or the anti-PD-L1 antibody and the anti-CTLA-4 antibody is formulated as a single composition, wherein the dose of the anti-PD-1 antibody or the anti-PD-L1 antibody and the dose of the anti-CTLA-4 antibody are combined at a ratio of 1:50, 1:40, 1:30, 1:20, 1:10. 1:5, 1:3, 1:1, 3:1, 5:1, 10:1, 20:1, 30:1, 40:1, or 50:1.

For a combination of an immunotherapeutic agent with other anti-cancer agents, these agents are typically administered at their approved dosages. Treatment is continued as long as clinical benefit is observed or until unacceptable toxicity or disease progression occurs. Nevertheless, in certain embodiments, the dosages of these anti-cancer agents administered are significantly lower than the approved dosage, i.e., a subtherapeutic dosage, of the agent is administered in combination with the immunotherapeutic agent.

In certain embodiments, the immunotherapeutic anti-cancer agent is administered in combination with the standard of care for the particular type of cancer. In further embodiments, the immunotherapeutic anti-cancer agent is administered in combination with chemotherapy, including 5-FU, etoposide and platinum-based drugs, for example carboplatin or cisplatin. In some embodiments, the immunotherapeutic anti-cancer agent is administered before, concurrently or after radiation therapy. In some embodiments, the immunotherapeutic anti-cancer agent is administered before, concurrently or after surgical resection.

Dosage and frequency vary depending on the half-life of the immunotherapeutic anti-cancer agent in the subject. In general, human antibodies show the longest half-life, followed by humanized antibodies, chimeric antibodies, and nonhuman antibodies. The dosage and frequency of administration can vary depending on whether the treatment is prophylactic or therapeutic. In prophylactic applications, a relatively low dosage is typically administered at relatively infrequent intervals over a long period of time. Some patients continue to receive treatment for the rest of their lives. In therapeutic applications, a relatively high dosage at relatively short intervals is sometimes required until progression of the disease is reduced or terminated, or until the patient shows partial or complete amelioration of symptoms of disease. Thereafter, the patient can be administered a prophylactic regime.

Actual dosage levels of the active ingredient or ingredients in the pharmaceutical compositions of the present invention can be varied so as to obtain an amount of the active ingredient which is effective to achieve the desired therapeutic response for a particular patient, composition, and mode of administration, without being unduly toxic to the patient. The selected dosage level will depend upon a variety of pharmacokinetic factors including the activity of the particular compositions of the present invention employed, the route of administration, the time of administration, the rate of excretion of the particular compound being employed, the duration of the treatment, other drugs, compounds and/or materials used in combination with the particular compositions employed, the age, sex, weight, condition, general health and prior medical history of the patient being treated, and like factors well known in the medical arts. A composition of the present invention comprising an immunotherapeutic agent can be administered via one or more routes of administration using one or more of a variety of methods well known in the art. As will be appreciated by the skilled artisan, the route and/or mode of administration will vary depending upon the desired results.

The immunotherapeutic agents of the present invention can be constituted in a composition, e.g., a pharmaceutical composition containing an antibody and a pharmaceutically acceptable carrier. As used herein, a "pharmaceutically acceptable carrier" includes any and all solvents, dispersion media, coatings, antibacterial and antifungal agents, isotonic and absorption delaying agents, and the like that are physiologically compatible. In one embodiment, the carrier for a composition containing an antibody is suitable for intravenous, intramuscular, subcutaneous, parenteral, spinal or epidermal administration (e.g., by injection or infusion), whereas the carrier for a composition containing a peptide, protein, small molecule, adjuvant, cytokine, oncolytic viruse, vaccine, bi-specific molecule and cellular therapeutic agent may be suitable for non-parenteral, e.g., oral, administration. A pharmaceutical composition of the invention can include one or more pharmaceutically acceptable salts, antioxidant, aqueous and non-aqueous carriers, and/or adjuvants such as preservatives, wetting agents, emulsifying agents and dispersing agents.

The glutamate modulating agents suitable for use in accordance with the present invention include any agents that: (a) promote the modulation, regulation, attenuation or potentiation of; (i) an ionotropic glutamate receptor; (ii) a metabotropic glutamate receptor; or (iii) a glutamate transporter; (b) inhibits glutamate release; or (c) modulates, regulates, attenuates or potentiates the metabolism of glutamate or glutamine. Ionotropic glutamate receptors include NMDA, AMPA and kainite. Metabotropic glutamate receptors include those from group 1 receptors including mGluR1 and mGluR5; group II including mGluR2 and mGluR3; and group III including mGluR4, mGluR6, mGluR7, and mGluR8. Glutamate transporters may be expressed in glia or in neurons. Preferably, the glutamate modulators: (i) normalize glutamate levels in the patient; (ii) attenuate or normalize glutamate release in the patient; or (iii) normalize, enhance or potentiates the uptake of glutamate in the patient.

The glutamate modulators may cause a reduction in the glutamine/glutamate levels or increase the cycling of glutamate by increasing the expression of excitatory amino acid transporters, causing a reduction in reduce proliferative and effector function.

Preferred glutamate modulators are selected from riluzole, memantine, n-acetlcysteine, amantadine, topiramate, pregabalin, lamotrigine, ketamine, s-ketamine, AZD8108, AZD 6765 (lanicemine), BHV-4157 (trigriluzole), dextromethorphan, AV-101, CERC-301, GLY-13, and pharmaceutically acceptable salts, prodrugs or analogs thereof. Riluzole is currently available in the market as RILUTEK® (riluzole) is available from Sanofi-Aventis, Bridgewater, NJ and has the structure shown below.

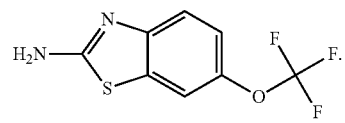

6-(trifluoromethoxy)benzothiazol-2-amine

The term "riluzole" also refers to all prodrugs, enantiomers, or derivatives and its pharmaceutically acceptable salts, except as otherwise noted. The term "riluzole prodrug" refers to a compound which is a derivative from riluzole with modification therein. A riluzole prodrug may also refer to a compound that is metabolized into an active form of riluzole by the body.

Certain preferred riluzole prodrugs have the structure:

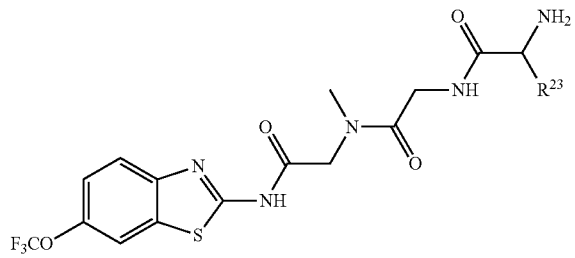

including enantiomers, diasteroemers, hydrates, solvates, pharmaceutically acceptable salts, and complexes thereof, wherein:

$R_{23}$ is selected from the group consisting H, $CH_3$, $CH_2CH_3$, $CH_2CH_2CH_3$, $CH_2CCH$, $CH(CH_3)_2$, $CH_2CH(CH_3)_2$, $CH(CH_3)CH_2CH_3$, $CH_2OH$, $CH_2OCH_2Ph$, $CH_2CH_2OCH_2Ph$, $CH(OH)CH_3$, $CH_2Ph$, $CH_2$(cyclohexyl), $CH_2$(4-OH-Ph), $(CH_2)_4NH_2$, $(CH_2)_3NHC(NH_2)NH$, $CH_2$(3-indole), $CH_2$(5-imidazole), $CH_2CO_2H$, $CH_2CH_2CO_2H$, $CH_2CONH_2$, and $CH_2CH_2CONH_2$. Those skilled in the art will recognize that similar or variant prodrugs can be made from other glutamate modulating agents. Such agents may be useful as part of the combination of the present invention.

One especially preferred glutamate modulator, trigriluzole, has the following formula:

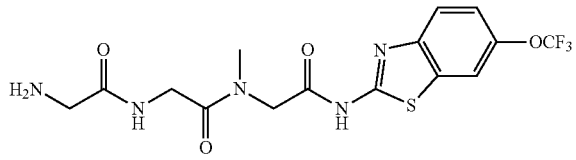

Prodrugs of riluzole are described, for example, in U.S. patent application Ser. No. 14/385,551, U.S. patent application Ser. No. 14/410,647, PCT Application Serial No. PCT/US2016/019773 and PCT Application Serial No.PCT/US2016/019787. Sublingual formulations of riluzole that provide stability and excellent properties are described in PCT Application Serial No. PCT/US2015/061106 and PCT Application Serial No. PCT/US2015/061114.

The glutamate modulating agents may be present as isotopically labeled forms of compounds detailed herein. Isotopically labeled compounds have structures depicted by the formulas given herein except that one or more atoms are replaced by an atom having a selected atomic mass or mass number. Examples of isotopes that can be incorporated into compounds of the disclosure include isotopes of hydrogen, carbon, nitrogen, oxygen, phosphorous, fluorine and chlorine, such as, but not limited to $^2$H (deuterium, D), $^3$H (tritium), $^{11}$C, $^{13}$C, $^{14}$C, $^{15}$N, $^{18}$F, $^{31}$P, $^{32}$P, $^{35}$S, Cl, I. Various isotopically labeled compounds of the present disclosure, for example those into which radioactive isotopes such as $^3$H, $^{13}$C and $^{14}$C are incorporated, are provided. Such isotopically labeled compounds may be useful in metabolic studies, reaction kinetic studies, detection or imaging techniques, such as positron emission tomography (PET) or single-photon emission computed tomography (SPECT) including drug or substrate tissue distribution assays or in radioactive treatment of subjects (e.g. humans). Also provided for isotopically labeled compounds described herein are any pharmaceutically acceptable salts, or hydrates, as the case may be.

In some variations, the compounds disclosed herein may be varied such that from 1 to "n" hydrogens attached to a carbon atom is/are replaced by deuterium, in which "n" is the number of hydrogens in the molecule. Such compounds may exhibit increased resistance to metabolism and are thus useful for increasing the half life of the compound when administered to a subject. See, for example, Foster, "Deuterium Isotope Effects in Studies of Drug Metabolism", *Trends Pharmacol. Sci.* 5(12):524-527 (1984). Such compounds are synthesized by means well known in the art, for example by employing starting materials in which one or more hydrogens have been replaced by deuterium.

Deuterium labeled or substituted therapeutic compounds of the disclosure may have improved drug metabolism and pharmacokinetics (DMPK) properties, relating to absorption, distribution, metabolism and excretion (ADME). Substitution with heavier isotopes such as deuterium may afford certain therapeutic advantages resulting from greater metabolic stability, for example increased in vivo half-life, reduced dosage requirements and/or an improvement in therapeutic index. An $^{18}$F labeled compound may be useful for PET or SPECT studies. Isotopically labeled compounds of this disclosure can generally be prepared by carrying out the procedures known to those skilled in the art by substituting a readily available isotopically labeled reagent for a non-isotopically labeled reagent. It is understood that deuterium in this context is regarded as a substituent in the compounds provided herein.

The concentration of such a heavier isotope, specifically deuterium, may be defined by an isotopic enrichment factor. In the compounds of this disclosure any atom not specifically designated as a particular isotope is meant to represent any stable isotope of that atom. Unless otherwise stated, when a position is designated specifically as "H" or "hydrogen", the position is understood to have hydrogen at its natural abundance isotopic composition.

The glutamate modulating agents of the present invention may be given orally, sublingually, intranasally, buccally, subcutaneously or in any other suitable means of delivery. The glutamate modulating agents may be in the form of a prodrug, which releases the agent in the body, a sustained release vehicle, a delayed release vehicle, or any other suitable delivery form. The glutamate modulating agent and the immunotherapy agent may be delivered simultaneously or sequentially. If the agents are delivered sequentially, either agent may be dosed first, and the separation of time may include finishing the dosing of one agent completely before commencing the dosage of the other or they may be intermingled in time. Typically, the glutamate modulating agent is administered at a time proximate to the administration of the immunotherapeutic anticancer agent, e.g., within 1 week, 1 day, 1 hour, 1 minute before or after the immunotherapeutic anticancer agent or simultaneously with the immunotherapeutic anticancer agent.

The dose of the glutamate modulating agent for use with the immunotherapeutic agent to be administered may depend on the subject to be treated inclusive of the age, sex, weight and general health condition thereof. In this regard, precise amounts of the agent(s) for administration will depend on the judgment of the practitioner. In determining the effective amount of the glutamate modulating agent and immunotherapeutic agent to be administered in the treatment or reducing of the conditions associated with the symptoms and disorders, the physician may evaluate clinical factors including symptoms severity or progression of the disorder. In some conditions, a rapid absorption of the glutamate modulating agent or immunotherapeutic agent may be desirable. The effective amount of the treatment will vary depending on the subject and disease state being treated, the severity of the affliction and the manner of administration, and may be determined routinely by one of ordinary skill in the art.

The glutamate modulating agent as part of the formulation for treating cancer or symptoms may be dosed at or below about 400 mg/day, at or below about 300 mg/day, at or below about 150 mg/day, at or below about 100 mg/day, at or below about 70 mg/day, at or below about 60 mg/day, at or below about 50 mg/day, at or below about 42.5 mg/day, at or below about 37.5 mg/day at or below about 35 mg/day, at or below about 20 mg/day, at or below about 17.5 mg/day, at or below about 15 mg/day, at or below about 10 mg/day, at or below about 5 mg/day, or at or below about 1 mg/day.

The pharmaceutical compositions of the present invention comprising the glutamate modulator typically also include other pharmaceutically acceptable carriers and/or excipients such as binders, lubricants, diluents, coatings, disintegrants, barrier layer components, glidants, coloring agents, solubility enhancers, gelling agents, fillers, proteins, co-factors, emulsifiers, solubilizing agents, suspending agents and mixtures thereof. A skilled artisan in the art would know what other pharmaceutically acceptable carriers and/or excipients could be included in the formulations according to the invention. The choice of excipients would depend on the characteristics of the compositions and on the nature of other pharmacologically active compounds in the formulation. Appropriate excipients are known to those skilled in the art (see Handbook of Pharmaceutical Excipients, fifth edition, 2005 edited by Rowe et al., McGraw Hill) and have been utilized to yield a novel sublingual formulation with unexpected properties.

Examples of pharmaceutically acceptable carriers that may be used in preparing the pharmaceutical compositions of the present invention may include, but are not limited to, fillers such as sugars, including lactose, sucrose, mannitol, or sorbitol; cellulose preparations such as maize starch, wheat starch, rice starch, potato starch, gelatin, gum tragacanth, methyl cellulose, hydroxypropyl methyl-cellulose, sodium carboxymethylcellulose, polyvinyl-pyrrolidone (PVP), talc, calcium sulphate, vegetable oils, synthetic oils, polyols, alginic acid, phosphate buffered solutions, emulsifiers, isotonic saline, pyrogen-free water and combinations thereof. If desired, disintegrating agents may be combined as well, and exemplary disintegrating agents may be, but not limited to, cross-linked polyvinyl pyrrolidone, agar, or alginic acid or a salt thereof such as sodium alginate. The compositions may be prepared by any of the methods of pharmacy but all methods include the step of bringing into association one or more chemical agents as described above with the carrier which constitutes one or more necessary ingredients. In general, the pharmaceutical compositions of the present invention may be manufactured in conventional methods known in the art, for example, by means of conventional mixing, dissolving, granulating, dragee-making, levigating, emulsifying, encapsulating, entrapping, lyophilizing processes and the like. Glutamate modulating agents such as riluzole and the pharmaceutically acceptable salts thereof can be formulated using pharmaceutically acceptable carriers well known in the art into dosages suitable for sublingual, intranasal or buccal administration. Such carriers enable the glutamate modulating agents to be formulated in dosage forms such as tablets, powders, pills, capsules, liquids, gels, films, syrups, slurries, suspensions, and the like.

Some of the glutamate modulating agents can be administered sublingually. PCT Application No. PCT/US2015/061106 and PCT Application No. PCT/US2015/061114 describe a sublingual formulation of riluzole, a preferred glutamate modulating agent. The sublingual formulation may be administered in an effective amount to a subject in need thereof. The subject may be an animal or human. When the glutamate modulating agent is prepared as a sublingual formulation, the sublingually administered chemical agent or the drug can diffuse into capillaries through mucous membrane under the tongue, and then enter venous circulation of the subject. As such, sublingual administration may have advantages over oral administration as allowing for direct or faster entry to venous circulation, without risks of degradation in gastrointestinal tract, alteration by drug metabolism in liver and the like.

A sublingual formulation useful in the present invention comprises an effective amount of riluzole or pharmaceutically acceptable salts, solvates, anomers, enantiomers, hydrates or prodrugs thereof. The formulation provides sufficient solubility for riluzole to be incorporated into the sublingual formulation at relatively large doses and sublingually delivered. The formulation is preferably a modified oral disintegrating formulation of riluzole. The excipients, including mannitol and gelatin, are blended, solubilized with water and deaerated before being mixed with the active pharmaceutical ingredient (or "API"), riluzole, which has been milled separately. Particle size of the API (D50) is less than about 2 microns. The mixture is lyophilized by flash freezing and then freeze-dried. The formulation has good oral palatability. The effective amount of glutamate modulating agent for the sublingual formulation useful in the present invention to achieve a lower therapeutic dose may be less than that of orally administered agent. Moreover, effective dose of the sublingual formulation of the glutamate modulating agent may be about 1 to 95% of that of the orally administered agent. To the extent that a sublingual formulation of the immunotherapeutic agent can be made, it may also have improved properties.

In one aspect of the invention, the glutamate modulator is provided in a sublingual formulation in a form of an orally dissolving or disintegrating tablet (ODT). The ODT as used herein may be prepared by mixing the glutamate modulating agent and/or the immunotherapeutic agent with water-soluble diluents and compressed in a tablet. A suspension comprising the active product may be prepared with appropriate excipients and the suspension may be dispensed into blister packs and freeze-dried. An exemplary freeze-dried preparation platform that could be used for the ODT is the ZYDIS® (Catalent, Somerset, NJ, USA) formulation. In particular, the excipients, including water, are blended and the glutamate modulating agent is separately milled to size and mixed with the excipients. The suspension then undergoes lyophilisation by flash freezing and freeze drying. Other methods of preparing ODTs may be used without limitation, and detailed description of general methods thereof have been disclosed, for example, in U.S. Pat. Nos. 5,631,023; 5,837,287; 6,149,938; 6,212,791; 6,284,270; 6,316,029; 6,465,010; 6,471,992; 6,471,992; 6,509,040; 6,814,978; 6,908,626; 6,908,626; 6,982,251; 7,282,217; 7,425,341; 7,939,105; 7,993,674; 8,048,449; 8,127,516; 8,158,152; 8,221,480; 8,256,233; and 8,313,768, each of which is incorporated herein by reference in its entirety. Some of the glutamate modulating agents can be administered sublingually. PCT Application No. PCT/US2015/061106 and PCT Application No. PCT/US2015/061114 describe a sublingual formulation of riluzole, a preferred glutamate modulating agent. The sublingual formulation may be administered in an effective amount to a subject in need thereof. The subject may be an animal or human.

The clinical or therapeutic effect of the glutamate modulating agent sublingually formulated may have an improved pharmacokinetic profile for the pharmaceutical agent as measured by standard testing parameters. When the glutamate modulating agent is administered sublingually, the Tmax, Cmax and AUC of the drug may be improved compared to the same dose of the orally administered version of the same compound. For example, the sublingual formulation of the glutamate modulating agent may have a greater Cmax than the orally administered glutamate modulating agent to provide a therapeutically beneficial effect. The sublingual formulation of the glutamate modulating agent may have an earlier or lesser Tmax than the orally administered glutamate modulating agent to provide a therapeutically beneficial effect and in some instances, a more rapid therapeutic effect. Alternatively, the sublingual formulation of the glutamate modulating agent may have a greater AUC per milligram of the agent than the orally administered glutamate modulating agent. In addition, as the glutamate modulating agent may make the immunotherapeutic agent more effective, lesser amounts of the immunotherapeutic agent may be needed to achieve the same results, with a lessening of the inherent side effects.

In one aspect, the invention provides a method of treating cancer which comprises administering sublingually an effective amount of glutamate modulating agent or pharmaceutically acceptable salts thereof and an anti-cancer immunotherapeutic agent, or pharmaceutically acceptable salts or prodrugs thereof to a subject in need thereof. The combination of these two drugs may be administered in a single dose as combined product, administered simultaneously using the same or distinct formats, or administered sequentially using the same or different forms of delivery. For example, if the can both be made into a tablet or part of a sublingual form, they can be administered together. Similarly, if the immunotherapeutic agent can only be administered by injection (bolus or intravenous), and the glutamate modulating agent can be administered in the same format, this could also be used for simultaneous or sequential administration. However, if the immunotherapeutic agent can only be delivered by injection (for example, if it is an antibody), and the glutamate modulating agent can be delivered as a tablet or sublingually, delivery of the two agents can take place by differing formats. Further details on the specific modes of administration of the immunotherapeutic agent and the glutamate modulating agent can be determined by those of ordinary skill in the art.

Identifying the subject in need of such treatment can be in the judgment of the subject or a health care professional and can be subjective (e.g., opinion) or objective (e.g., measurable by a test or diagnostic method). The identified subject may be an animal or human in need thereof, particularly a human. Such treatment will be suitably administered to subjects, particularly humans, suffering from the disease.

The therapeutic effect of the combination product, particularly as it applies to treating symptoms, may be evident to occur within about a few minutes to about an hour after administration thereof. In particular, the therapeutic effect may begin within about 1 minute, within about 2 minutes, within about 3 minutes, within about 4 minutes, within about 5 minutes, within about 6 minutes, within about 7 minutes, within about 8 minutes, within about 9 minutes, within about 10 minutes, within about 11 minutes, within about 12 minutes, within about 13 minutes, within about 14 minutes, within about 15 minutes, within about 16 minutes, within about 17 minutes, within about 18 minutes, within about 20 minutes, within about 60 minutes, or within about 90 minutes after administration. However, long term cure or amelioration of the disease may not occur for weeks or months after administration.

The effects on the symptoms may be maintained for about 1 hour, for about 2 hours, for about 3 hours, for about 4 hours, for about 5 hours, for about 6 hours m for about 7 hours, for about 8 hours, for about 9 hours, for about 10 hours, for about 12 hours, for about 14 hours, for about 16 hours, for about 18 hours, for about 20 hours, for about 22 hours, for about 24 hours, for about 2 days, or for about 3 days or more after administration thereof. Hopefully, once the long term effects on the disease state is achieved, the disease, and the symptoms, will be eliminated permanently.

Typical dosage frequencies for the glutamate modulating agents include once a day, twice a day, three times a day, four times a day, once every other day, once a week, twice a week, three times a week, four times a week, once every two weeks, once or twice monthly, and the like.

In certain embodiments, the immunotherapy therapy of the present invention (e.g., administration of an anti-PD-1 antibody or an anti-PD-L1 antibody and, optionally, another anti-cancer agent) in combination with a glutamate modulator effectively increases the duration of survival of the subject. In some embodiments, the combination therapy of the present invention increases the duration of survival of the subject in comparison to standard-of-care therapies. In certain embodiments, the therapy of the invention increases the overall survival of the subject. In some embodiments, the subject exhibits an overall survival of at least about 10 months, at least about 11 months, at least about 12 months, at least about 13 months, at least about 14 months at least about 15 months, at least about 16 months, at least about 17 months, at least about 18 months, at least about 19 months, at least about 20 months, at least about 21 months, at least about 22 months, at least about 23 months, at least about 2 years, at least about 3 years, at least about 4 years, or at least about 5 years after the administration. In some embodiments, the duration of survival or the overall survival of the subject is increased by at least about 5%, at least about 10%, at least about 15%, at least about 20%, at least about 25%, at least about 30%, at least about 40%, at least about 50% or at least about 75% when compared to another subject treated with only a standard-of-care therapy. In other embodiments, the duration of survival or the overall survival of the subject is increased by at least about 1 month, at least about 2 months, at least about 3 months, at least about 4 months, at least about 6 months, at least about 1 year, at least about eighteen months, about least about 2 years, at least about 3 years, at least about 4 years or at least about 5 years when compared to another subject treated with only a standard-of-care therapy.

In certain embodiments, the combination therapy of the present invention effectively increases the duration of progression free survival of the subject. For example, the progression free survival of the subject is increased by at least about 2 weeks, at least about 1 month, at least about 2 months, at least about 3 months, at least about 4 months, at least about 6 months, or at least about 1 year when compared to another subject treated with only standard-of-care therapy. In certain embodiments, after the administration of an immunotherapeutic agent (e.g., anti-PD-1 antibody or anti-PD-L1 antibody therapy) in combination with a glutamate modulator, the subject exhibits an overall response rate of at least about 30%, 35%, 36%, 37%, 39%, 40%, 45%, or 50% compared to the response rate after administration of a standard-of-care therapy.

In certain embodiments, the combination therapy of the present invention provides an improved treatment response which may, for example, be one or more of overall survival, quality of life, overall response rate, duration of response, progression free survival, patient reported outcome, minimal residual disease or immune response.

A preferred glutamate modulating agent is riluzole and a preferred immunotherapy agent is a checkpoint inhibitor such as an anti-PD-1 antibody. It appears that the glutamate modulators may make the cancer cells more susceptible to the anti-cancer agents such as immunotherapeutic agents. Further, the glutamate modulators may sensitize the patient to render the treatment with the immunotherapeutic agents more effective.

Also within the scope of the present invention are kits comprising an immunotherapeutic agent (e.g., an anti-PD-1 antibody or and anti-PD-L1 antibody) and/or a glutamate modulator (e.g., riluzole) and, optionally, another anti-cancer agent for therapeutic uses. Kits typically include a label indicating the intended use of the contents of the kit and instructions for use. The term label includes any writing, or recorded material supplied on or with the kit, or which otherwise accompanies the kit. In certain embodiments for treating human patients, the kit comprises an anti-human PD-1 antibody or anti-human PD-L1 antibody disclosed herein, e.g., nivolumab or pembrolizumab. In other embodiments, the kit comprises an anti-human CTLA-4 antibody disclosed herein, e.g., ipilimumab or tremelimumab. In other embodiments, the kit comprises a glutamate modulating agent, e.g., riluzole or trigrilozole.

A variety of solid malignancies have been shown to overexpress phosphate-dependent glutaminase (GLS), which converts glutamine to glutamate further emphasizing the role of glutamine in cancer metabolism. However, glutamate is a key nitrogen "waste" bank and critical in a variety of cellular metabolic pathways. As such, reduction in glutamine/glutamate levels to immune cells may reduce proliferative and effector function, limiting an anti-tumor immune mediated response. While this effect is clear for GLS producing tumor cells, glutamate receptors are found on a number of other tumor cells and it is believed that this combination therapy could be effective for those cells as well.

EXAMPLES

The following examples illustrate the invention and are not intended to limit the scope of the invention. In some examples, abbreviations are used which are known to those skilled in the art or are readily accessible from the documents cited in the examples, e.g., the Summary of Product Characteristics published by the European Medicines Agency.

Example 1

In this Example, the effects of the combination of a glutamate modulator, BHV-4157, in combination with an immunotherapeutic agent, anti-PD-1, were compared to either alone in a glioma model substantially as decribed in Zeng, J., et al., Int J Radiat Oncol Biol Phys., 2013 Jun. 1; 86(2):343-349, portions of which are reproduced below.

Cells

GL261-Luc cells are grown in Dulbecco's Modified Eagle Medium (DMEM)+10% fetal bovineserum+1% penicillinstreptomycin at 37° C. in a humidified incubator maintained at 5% CO and 5% $O_2$ (Gibco).

Tumor Model

Female C57BL/6J mice (Harlan), 4 to 6 weeks old or 6 to 8 weeks old, are used for orthotopic glioma experiments as described in Sonabend A M, Velicu S, Ulasov IV, et al. A safety and efficacy study of local delivery of interleukin 12 transgene by PPC polymer in a model of experimental glioma. Anticancer Drugs. 2008;19:133-142. To establish syngeneic gliomas, 130,000 GL261-Luc cells are stereotactically injected in a 1 µl volume into the left striatum over 1 minute into the following coordinates: 1 mm anterior, 1 mm lateral from bregma, and 3 mm deep from the cortical surface. Tumor burden is monitored by luciferase imaging on days 7, 21 and 35 after implantation, and the mice are randomly allocated into treatment arms based on tumor radiance, so that the average tumor radiance in each group is roughly equivalent. The animals are euthanized when they show predetermined signs of neurologic deficits (failure to ambulate, weight loss >20% body mass, lethargy, hunched posture). The tumor take rate is 100%. Each arm has 6 to 10 mice in survival experiments. All experiments are repeated at least in triplicate.

Anti-PD-1 Antibodies

Hamster antimurine PD-1 monoclonal antibody producing hybridoma G4 are used to produce antibodies as described in Hirano F, Kaneko K, Tamura H, et al. Blockade of B7-H1 and PD-1 by monoclonal antibodies potentiates cancer therapeutic immunity. Cancer Res. 2005;65:1089-1096.

Specific Protocol

Female C57BL/6J mice, 4 to 6 weeks old, were implanted intracranially in the left striatum with 130,000 GL261 cells each. The mice were housed and maintained according to the institutional Animal Care and Use Committee protocol in the Johns Hopkins University Animal Facility. The mice were imaged by bioluminescent IVIS® imaging (Perkin Elmer) at day 7, 21, and 35 to assess tumor burden and randomly assigned to groups, 10 mice per arm, as follows:

1. Control
2. anti-PD-1
3. Trigriluzole 15 mg/kg
4. Trigriluzole 30 mg/kg
5. Trigriluzole 45 mg/kg
6. anti-PD-1+Trigriluzole 15 mg/kg
7. anti-PD-1+Trigriluzole 30 mg/kg
8. anti-PD-1+Trigriluzole 45 mg/kg The protocol is shown in FIG. 2.

Day 0 represents the date of intracranial implantation. Control arm 1 received no treatment. Control arm 2 received αPD-1 alone at a dose of 200 µg/animal via intraperitoneal injection on days 10, 12, 14. Control arms 3, 4 and 5 received BHV-4157 alone at doses of 15, 30 and 45 mg/kg (respectively) via intraperitoneal injection daily beginning on day 10. Control arms 6, 7 and 8 received BHV-4157 at doses of 15, 30 and 45 mg/kg (respectively) via intraperitoneal injection daily beginning on day 10 and αPD-1 at a dose of 200 µg/animal via intraperitoneal injection on days 10, 12, 14.

The treatment was terminated when mice showed no tumor burden via IVIS imaging. Animals were euthanized according to humane endpoints including central nervous system disturbances, hunched posture, lethargy, weight loss, and inability to ambulate.

The purpose of the experiment was to see if the combination therapy was provided a benefit over either therapy alone. The results are shown in FIG. 1. As is evident from FIG. 1, the combination therapy is substantially better than any of the individual therapies and that the effects are not merely additive but appear synergistic. Thus, it appears that the glutamate modulators effect on glutamate/glutamine metabolism weakens the tumor cells and makes the anti-PD-1 antibody more effective. Quite surprisingly, in accordance with the present invention, the percentage survival of mice at about 30, 40 and 60 days after implantation was about 2 times, or greater, the percent survival for the mice treated with the glutamate modulator in combination with the immunotherapeutic anti-cancer agent as compared to the immunotherapeutic anti-cancer agent alone. Table 1 below shows data from Example 1.

TABLE 1

PERCENT SURVIVAL OF MICE AFTER TUMOR IMPLANTATION

| Days after Tumor Implantation | Arm 1 Control | Arm 2 PD-1 | Arm 3 BHV-4157 15 mg/kg | Arm 4 BHV-4157 30 mg/kg | Arm 5 BHV-4157 45 mg/kg | Arm 6 PD-1 + BHV-4157 15 mg/kg | Arm 7 PD-1 + BHV-4157 30 mg/kg | Arm 8 PD-1 + BHV-4157 45 mg/kg |
|---|---|---|---|---|---|---|---|---|
| 0 | 100 | 100 | 100 | 100 | 100 | 100 | 100 | 100 |
| 18 | 80 | | | | | | | |
| 19 | 70 | | | | | | | |
| 20 | 40 | | | | | 90 | | |
| 21 | 30 | | 90 | 90 | 90 | | | |
| 22 | | 90 | 80 | | 80 | | | |
| 23 | 20 | 80 | 70 | 70 | 70 | | | |
| 24 | 10 | | 50 | 50 | 60 | | | 90 |
| 25 | | 70 | | | 50 | 80 | 80 | |
| 26 | 0 | 50 | 30 | 30 | | | 70 | |

TABLE 1-continued

PERCENT SURVIVAL OF MICE AFTER TUMOR IMPLANTATION

| Days after Tumor Implantation | Arm 1 Control | Arm 2 PD-1 | Arm 3 BHV-4157 15 mg/kg | Arm 4 BHV-4157 30 mg/kg | Arm 5 BHV-4157 45 mg/kg | Arm 6 PD-1 + BHV-4157 15 mg/kg | Arm 7 PD-1 + BHV-4157 30 mg/kg | Arm 8 PD-1 + BHV-4157 45 mg/kg |
|---|---|---|---|---|---|---|---|---|
| 27 |  | 40 | 20 |  | 20 | 70 |  |  |
| 28 |  | 30 | 10 |  | 10 |  |  |  |
| 29 |  |  |  | 20 | 0 | 60 |  |  |
| 30 |  |  |  |  |  |  |  | 80 |
| 34 |  |  |  | 10 |  |  | 60 |  |
| 36 |  |  | 0 |  |  |  |  |  |
| 43 |  |  |  |  |  |  |  | 70 |
| 60 |  | 30 |  | 10 |  | 60 | 60 | 70 |

From Table 1, it can be seen that by day 26, the mice in Arm 1 (Control) had 0% survival, the mice in Arm 2 (PD-1) had 50% survival and the mice in Arms 6, 7 and 8 had at least 70 to 80% survival. Accordingly, at day 26, the Mouse Survival Ratio ($MSR_{26}$) was about 1.4 to 1.6 (i.e., 70/50 and 80/50). At day 28, the mice in Arm 1 (Control) had 0% survival, the mice in Arm 2 (PD-1) had 30% survival and the mice in Arms 6, 7 and 8 had at least 60 to 80% survival. Accordingly, at day 28, the Mouse Survival Ratio ($MSR_{28}$) was about 2.0 to 2.6 (i.e., 60/30 and 80/30). At day 60, the mice in Arm 1 (Control) had 0% survival, the mice in Arm 2 (PD-1) had 30% survival and the mice in Arms 6, 7 and 8 had 60 to 70% survival. Accordingly, at day 60, the Mouse Survival Ratio ($MSR_{60}$) was about 2.0 to 2.3 (i.e., 60/30 and 70/30). Preferably, in accordance with the present invention, the Mouse Survival Ratio is at least 1.4, more preferably at least 1.6 when measured at 26 days after tumor implantation ($MSR_{26}$). Preferably, in accordance with the present invention, the Mouse Survival Ratio is at least 2.0, more preferably at least 2.6 when measured at 28 days after tumor implantation ($MSR_{28}$). Preferably, in accordance with the present invention, the Mouse Survival Ratio is at least 2.0, more preferably at least 2.3 when measured at 60 days after tumor implantation ($MSR_{60}$). Preferably, in accordance with the present invention, the Mouse Survival Ratio measured at a time when the untreated mice reach 0% survival, or thereafter until a time of 60 days after tumor implantation, is at least 1.4, at least 1.6, at least 2.0, at least 2.3 or at least 2.6. Typically, combination therapy, i.e., an immunotherapeutic anti-cancer agent and a glutamate modulating agent, in accordance with the present invention will provide a Mouse Survival Ratio of at least 2.0, more typically at least 2.3 (measured at day 60, $MSR_{60}$).

Example 2

The following illustrates an example of how a glutamate modulator of the present invention may be used in combination therapy with KEYTRUDA™ (pembrolizumab), available from Merck & Co., Inc., Whitehouse Station, NJ, USA. For additional information, please see HIGHLIGHTS OF PRESCRIBING INFORMATION for KEYTRUDA (pembrolizumab) for injection, for intravenous use KEYTRUDA (pembrolizumab) injection, for intravenous use (uspi-mk3475-iv-1703r007) ("KETRUDA Package Insert").

According to the KETRUDA Package Insert, KEYTRUDA is a programmed death receptor-1 (PD-1)-blocking antibody indicated for the treatment of: —patients with unresectable or metastatic melanoma. —patients with metastatic NSCLC whose tumors have high PD-L1 expression [(Tumor Proportion Score (TPS)≥50%)] as determined by an FDA-approved test, with no EGFR or ALK genomic tumor aberrations, and no prior systemic chemotherapy treatment for metastatic NSCLC. —patients with metastatic NSCLC whose tumors express PD-L1 (TPS≥1%) as determined by an FDA-approved test, with disease progression on or after platinum-containing chemotherapy. Patients with EGFR or ALK genomic tumor aberrations should have disease progression on FDA-approved therapy for these aberrations prior to receiving KEYTRUDA. —patients with recurrent or metastatic HNSCC with disease progression on or after platinum-containing chemotherapy. This indication is approved under accelerated approval based on tumor response rate and durability of response. Continued approval for this indication may be contingent upon verification and description of clinical benefit in the confirmatory trials. —adult and pediatric patients with refractory cHL, or who have relapsed after 3 or more prior lines of therapy. This indication is approved under accelerated approval based on tumor response rate and durability of response. Continued approval for this indication may be contingent upon verification and description of clinical benefit in the confirmatory trials.

In the Summary of Product Characteristics for KETRUDA, published by the European Medicines Agency, the following clinical study is disclosed. This study was not conducted by the Applicant, but is presented for illustrative purposes.

Melanoma

KEYNOTE-006: Controlled Trial in Melanoma Patients Naïve to Treatment with Ipilimumab.

The safety and efficacy of pembrolizumab were investigated in KEYNOTE-006, a multicentre, controlled, Phase III study for the treatment of advanced melanoma in patients who were naïve to ipilimumab. Patients were randomised (1:1:1) to receive pembrolizumab 10 mg/kg every 2 (n=279) or 3 weeks (n=277) or ipilimumab 3 mg/kg every 3 weeks (n=278). Patients with BRAF V600E mutant melanoma were not required to have received prior BRAF inhibitor therapy. Patients were treated with pembrolizumab until disease progression or unacceptable toxicity. Clinically stable patients with initial evidence of disease progression were permitted to remain on treatment until disease progression was confirmed. Assessment of tumour status was performed at 12 weeks, then every 6 weeks through week 48, followed by every 12 weeks thereafter. Of the 834 patients, 60% were male, 44% were ≥65 years (median age was 62 years [range 18-89]) and 98% were white. Sixty-five percent of patients had M1c stage, 9% had a history of brain metastases, 66% had no and 34% had one prior therapy. Thirty-one percent had an ECOG Performance Status of 1, 69% had ECOG Performance Status of 0 and 32% had elevated LDH. BRAF mutations were reported in 302 (36%) patients. Among patients with BRAF mutant tumours, 139 (46%) were previously treated with a BRAF inhibitor. The primary efficacy outcome measures were progression free survival (PFS; as assessed by Integrated Radiology and Oncology Assessment [IRO] review using Response Evaluation Criteria in Solid Tumours [RECIST], version 1.1) and overall survival (OS). Secondary efficacy outcome measures were overall response rate (ORR) and response duration. Table 2 summarises key efficacy measures in patients naïve to treatment with ipilimumab.

TABLE 2

Response to pembrolizumab 10 mg/kg every 2 or 3 weeks in patients with ipilimumab naïve advanced melanoma in KEYNOTE-006*

| Endpoint | Pembrolizumab 10 mg/kg every 3 weeks n = 277 | Pembrolizumab 10 mg/kg every 2 weeks n = 279 | Ipilimumab 3 mg/kg every 3 weeks n = 278 |
|---|---|---|---|
| OS | | | |
| Number (%) of patients with event | 92 (33%) | 85 (30%) | 112 (40%) |
| Hazard ratio* (95% CI) | 0.69 (0.52, 0.90) | 0.63 (0.47, 0.83) | — |
| p-Value† | 0.00358 | 0.00052 | — |
| Median in months (95% CI) | Not reached (NA, NA) | Not reached (NA, NA) | Not reached (13, NA) |
| PFS | | | |
| Number (%) of patients with event | 157 (57%) | 157 (56%) | 188 (68%) |
| Hazard ratio* (95% CI) | 0.58 (0.47, 0.72) | 0.58 (0.46, 0.72) | — |
| p-Value† | <0.00001 | <0.00001 | — |
| Median in months (95% CI) | 4.1 (2.9, 6.9) | 5.5 (3.4, 6.9) | 2.8 (2.8, 2.9) |
| Best overall response | | | |
| ORR % (95% CI) | 33% (27, 39) | 34% (28, 40) | 12% (8, 16) |
| Complete response % | 6% | 5% | 1% |
| Partial response % | 27% | 29% | 10% |
| Response duration‡ | | | |
| Median in months (range) | Not reached (1.4+, 8.1+) | 8.3 (1.4+, 8.3) | Not reached (1.1+, 79+) |
| % ongoing | 97% | 89% | 88% |

*Hazard ratio (pembrolizumab compared to ipilimumab) based on the stratified Cox proportional hazard model
†Based on stratified Log rank test
‡Based on patients with a best overall response as confirmed complete or partial response
NA = not available In accordance with the present invention, patients participating in a study such as described above may be treated with a glutamate modulating agent, e.g., riluzole or its prodrug BHV-4157 (2-Amino-N-{[methyl({[6-(trifluoromethoxy)-1,3-benzo thiazol-2-yl]carbamoyl}methyl)carbamoyl]methyl}acetamide) in combination therapy. The specific treatment regimen can be determined by one skilled in the art. However, for illustrative purposes, the following may be considered in designing the treatment regimen. Abbreviations used in the following are commonly known to those skilled in the art.

Considerations for Use of Glutamate Modulating Agents in Combination with PD-1 Blocking Antibodies Using BHV-4157 and Pembrolizumab as an Illustration Protocol Synopsis

| | |
|---|---|
| Route of administration: | PO (BHV-4157) |
| | IV (pembrolizumab) |
| Trial Blinding: | None |
| Trial Treatments: | BHV-4157 + pembrolizumab |
| Treatment Groups: | Single-arm dose escalation study of BHV-4157 with pembrolizumab, followed by cohort of BHV-4157 at the maximum tolerated dose (MTD) |
| Study Design: | The study will combine BHV-4157 in escalating dose cohorts with a constant dose of pembrolizumab to identify the MTD of BHV-4157. |

-continued

| | |
|---|---|
| Study Objectives: | To determine the safety and preliminary efficacy of BHV-4157 in combination with pembrolizumab in patients with advanced cancer. |
| Research Hypotheses: | Combination treatment with BHV-4157 + anti-PD-1 antibody will be tolerable and demonstrate preliminary efficacy. |
| Key Inclusion Criteria: | Patients must have histologically confirmed solid malignancy (excluding lymphoma) that is metastatic or unresectable for which there is reasonable expectation of response to pembrolizumab. |
| | Measurable or evaluable disease |
| | ECOG 0-2 |
| | Adequate organ function |
| | No systemic immunosuppressive medications |
| | No active, untreated CNS metastases |

| | |
|---|---|
| Criteria for Evaluation: | Toxicity will be evaluated by CTAC v 4.0 Efficacy will be evaluated by RECIST version 1.1 |
| Number of Subjects: | 12 to 27 |
| Statistics: | Semi-Bayesian modified toxicity probability interval (mTPI) method for Phase I dose escalation |
| Correlative Studies: | Pre- and post-treatment tumor and blood samples will be analyzed for Immune: decrease in Tregs, MDSC, TAM, increase in TILs, increase in PD-L1 expression, increase in immune-related gene expression profile Angiogenesis: decrease in IL-8 and VEGF Signal transduction in key metabolic pathways: decrease in MAPK, ERK, PI3K/AKT, effects onWNT/beta-catenin/ATF3/CCL4 Exosomes: Decreased exosome formation, decreased production of CCL4 and M-CSF |
| Estimated Enrollment Period: | 1.5 years |
| Duration of Subject Participation: | Up to 1 year |
| Estimated Duration of Trial: | 2 years |

Treatment—The subjects could be treated with daily oral dosing of BHV-4157 with IV treatment with pembrolizumab at predetermined intervals, such as, for example, weeks 1, 3, 5, 7, 9 and 11. The primary endpoint is the maximum tolerated dose (MTD) of BHV-4157 and the recommended phase 2 dose (RP2D). The secondary endpoints include:
  objective response rate (ORR)
  adverse event type, severity and frequency
  survival time (OS), landmark survival rates at 1 and 2 years
  duration of response for responding patients
  time to progressive disease (PFS)
  time to treatment failure
  time to next therapy or death (TTNTD)
  freedom from new metastases
  correlative science: changes in the tumor microenvironment and peripheral blood in the following categories:
    TILs and PD-L1 expression
    Immune cell phenotypes and gene expression
    Angiogenesis markers
    Metabolic effector molecules
    Exosomal formation Upon completion of the study described above, additional studies to determine efficacy, dosage refinements, side effects and the like can be conducted to identify useful treatments for patients undergoing immune-oncology therapy in combination with a glutamate modulating agent.

Example 3

The following illustrates an example of how a glutamate modulator of the present invention may be used in combination therapy with OPDIVO® (nivolumab), available from Bristol-Myers Squibb Company Princeton, NJ USA. For additional information, please see HIGHLIGHTS OF PRESCRIBING INFORMATION for OPDIVO (nivolumab) injection, for intravenous use (1506US1700258-01-01) ("OPDIVO Package Insert").

According to the OPDIVO Package Insert, OPDIVO is a programmed death receptor-1 (PD-1) blocking antibody indicated for the treatment of patients with: •BRAF V600 wild-type unresectable or metastatic melanoma, as a single agent. •BRAF V600 mutation-positive unresectable or metastatic melanoma, as a single agent. This indication is approved under accelerated approval based on progression-free survival. Continued approval for this indication may be contingent upon verification and description of clinical benefit in the confirmatory trials. •Unresectable or metastatic melanoma, in combination with ipilimumab. This indication is approved under accelerated approval based on progression-free survival. Continued approval for this indication may be contingent upon verification and description of clinical benefit in the confirmatory trials. •Metastatic non-small cell lung cancer and progression on or after platinum-based chemotherapy. Patients with EGFR or ALK genomic tumor aberrations should have disease progression on FDA-approved therapy for these aberrations prior to receiving OPDIVO. •Advanced renal cell carcinoma who have received prior anti-angiogenic therapy. •Classical Hodgkin lymphoma that has relapsed or progressed after autologous hematopoietic stem cell transplantation (HSCT) and post-transplantation brentuximab vedotin. This indication is approved under accelerated approval based on overall response rate. Continued approval for this indication may be contingent upon verification and description of clinical benefit in confirmatory trials. •Recurrent or metastatic squamous cell carcinoma of the head and neck with disease progression on or after a platinum-based therapy. •Locally advanced or metastatic urothelial carcinoma who: •have disease progression during or following platinum-containing chemotherapy •have disease progression within 12 months of neoadjuvant or adjuvant treatment with platinum-containing chemotherapy. This indication is approved under accelerated approval based on tumor response rate and duration of response. Continued approval for this indication may be contingent upon verification and description of clinical benefit in confirmatory trials.

In the Summary of Product Characteristics for OPDIVO, published by the European Medicines Agency, the following clinical study is disclosed. This study was not conducted by the Applicant, but is presented for illustrative purposes.

Melanoma—Randomised Phase 3 Study Vs. Dacarbazine (CA209066)

The safety and efficacy of nivolumab 3 mg/kg for the treatment of advanced (unresectable or metastatic) melanoma were evaluated in a phase 3, randomised, double-blind study (CA209066). The study included adult patients (18 years or older) with confirmed, treatment-naive, Stage III or IV BRAF wild-type melanoma and an ECOG performance-status score of 0 or 1. Patients with active autoimmune disease, ocular melanoma, or active brain or leptomeningeal metastases were excluded from the study. A total of 418 patients were randomised to receive either nivolumab (n=210) administered intravenously over 60 minutes at 3 mg/kg every 2 weeks or dacarbazine (n=208) at 1000 mg/m2 every 3 weeks. Randomisation was stratified by tumour PD-L1 status and M stage (M0/M1a/M1b versus M1c). Treatment was continued as long as clinical benefit was observed or until treatment was no longer tolerated. Treatment after disease progression was permitted for patients who had a clinical benefit and did not have substantial adverse effects with the study drug, as determined by the investigator. Tumour assessments, according to the Response Evaluation Criteria in Solid Tumours (RECIST), version 1.1, were conducted 9 weeks after randomisation and continued every 6 weeks for the first year and then every 12 weeks thereafter. The primary efficacy outcome measure was overall survival (OS). Key secondary efficacy outcome measures were investigator-assessed PFS and objective response rate (ORR). Baseline characteristics were balanced between the two groups. The median age was 65 years (range: 18-87), 59% were men, and 99.5% were white. Most patients had ECOG performance score of 0 (64%) or 1 (34%). Sixty-one percent of patients had M1c stage disease at study entry. Seventy-four percent of patients had cutaneous melanoma, and 11% had mucosal melanoma; 35% of patients had PD-L1 positive melanoma (>5% tumour cell membrane expression). Sixteen percent of patients had received prior adjuvant therapy; the most common adjuvant treatment was interferon (9%). Four percent of patients had a history of brain metastasis, and 37% of patients had a baseline LDH level greater than ULN at study entry. Efficacy results are shown in Table 3.

nation therapy with YERVOY® (ipilimumab), available from Bristol-Myers Squibb Company Princeton, NJ USA. For additional information, please see HIGHLIGHTS OF PRESCRIBING INFORMATION for YERVOY (ipilimumab) injection, for intravenous use (1506US1700258-01-01) ("YERVOY Package Insert").

According to the YERVOY Package Insert, YERVOY is a human cytotoxic T-lymphocyte antigen 4 (CTLA-4)-blocking antibody indicated for: •Treatment of unresectable or metastatic melanoma. •Adjuvant treatment of patients with cutaneous melanoma with pathologicinvolvement of regional lymph nodes of more than 1 mm who have undergone complete resection, including total lymphadenectomy.

TABLE 3

Efficacy Results (CA209066)

|  | nivolumab (n = 210) |  | dacarbazine (n = 208) |
| --- | --- | --- | --- |
| Overall survival |  |  |  |
| Events | 50 (23.8) |  | 96 (46.2) |
| Hazard ratio |  | 0.42 |  |
| 99.79% CI |  | (0.25, 0.73) |  |
| 95% CI |  | (0.30, 0.60) |  |
| p-value |  | <0.0001 |  |
| Median (95% CI) | Not reached |  | 10.8 (9.33, 12.09) |
| Rate (95% CI) |  |  |  |
| At 6 months | 84.1 (78.3, 88.5) |  | 71.8 (64.9, 77.6) |
| At 12 months | 72.9 (65.5, 78.9) |  | 42.1 (33.0, 50.9) |
| Progression-free survival |  |  |  |
| Events | 108 (51.4) |  | 163 (78.4) |
| Hazard ratio |  | 0.43 |  |
| 95% CI |  | (0.34, 0.56) |  |
| p-value |  | <0.0001 |  |
| Median (95% CI) | 5.1 (3.48, 10.81) |  | 2.2 (2.10, 2.40) |
| Rate (95% CI) |  |  |  |
| At 6 months | 48.0 (40.8, 54.9) |  | 18.5 (13.1, 24.6) |
| At 12 months | 41.8 (34.0, 49.3) |  | NA |
| Objective response | 84 (40.0%) |  | 29 (13.9%) |
| (95% CI) | (33.3, 47.0) |  | (9.5, 19.4) |
| Odds ratio |  | 4.06 |  |
| (95% CI) |  | (2.52, 6.54) |  |
| p-value |  | <0.0001 |  |
| Complete response (CR) | 16 (7.6%) |  | 2 (1.0%) |
| Partial response (PR) | 68 (32.4%) |  | 27 (13.0%) |
| Stable disease (SD) | 35 (16.7%) |  | 46 (22.1%) |
| Median duration of response |  |  |  |
| Months (range) | Not reached (0⁺-12.5⁺) |  | 6.0 (1.1-10.0⁺) |
| Median time to response |  |  |  |
| Months (range) | 2.1 (1.2-7.6) |  | 2.1 (1.8-3.6) |

"⁺"deontes a censored observation.

In accordance with the present invention, patients participating in a study such as described above may be treated with a glutamate modulating agent, e.g., riluzole or its prodrug BHV-4157 (2-Amino-N-{[methyl({[6-(trifluoromethoxy)-1,3-benzo thiazol-2-yl]carbamoyl}methyl)carbamoyl]methyl}acetamide). The treatment regimen using the glutamate modulating agent may, for example, be as identified described in Example 2.

Example 4

The following illustrates an example of how a glutamate modulator of the present invention may be used in combi- In the Summary of Product Characteristics for YERVOY, published by the European Medicines Agency, the following clinical study is disclosed. This study was not conducted by the Applicant, but is presented for illustrative purposes. MDX010-20

A Phase 3, double-blind study enrolled patients with advanced (unresectable or metastatic) melanoma who had previously been treated with regimens containing one or more of the following: IL-2, dacarbazine, temozolomide, fotemustine, or carboplatin. Patients were randomized in a 3:1:1 ratio to receive ipilimumab 3 mg/kg+an investigational gp100 peptide vaccine (gp100), ipilimumab 3 mg/kg monotherapy, or gp100 alone. All patients were HLA-A2*0201 type; this HLA type supports the immune presentation of gp100. Patients were enrolled regardless of their baseline BRAF mutation status. Patients received ipilimumab every 3 weeks for 4 doses as tolerated (induction therapy). Patients with apparent tumour burden increase before completion of the induction period were continued on induction therapy as tolerated if they had adequate performance status. Assessment of tumour response to ipilimumab was conducted at approximately Week 12, after completion of induction therapy. Additional treatment with ipilimumab (re-treatment) was offered to those who developed PD after initial clinical response (PR or CR) or after SD (per the modified WHO criteria)>3 months from the first tumour assessment. The primary endpoint was OS in the ipilimumab+ gp100 group vs. the gp100 group. Key secondary endpoints were OS in the ipilimumab+ gp100 group vs. the ipilimumab monotherapy group and in the ipilimumab monotherapy group vs. the gp100 group. A total of 676 patients were randomized: 137 to the ipilimumab monotherapy group, 403 to the ipilimumab+gp100 group, and 136 to the gp100 alone group. The majority had received all 4 doses during induction. Thirty-two patients received re-treatment: 8 in the ipilimumab monotherapy group, 23 in the ipilimumab+ gp100 group, and 1 in the gp100 group. Duration of follow-up ranged up to 55 months. Baseline characteristics were well balanced across groups. The median age was 57 years. The majority (71-73%) of patients had M1c stage disease and 37-40% of patients had an elevated lactate dehydrogenase (LDH) at baseline. A total of 77 patients had a history of previously treated brain metastases. The ipilimumab-containing regimens demonstrated a statistically significant advantage over the gp100 control group in OS. The hazard ratio (HR) for comparison of OS between ipilimumab monotherapy and gp100 was 0.66 (95% CI: 0.51, 0.87; p=0.0026). 17 By subgroup analysis, the observed OS benefit was consistent within most of the subgroups of patients (M [metastases]-stage, prior interleukin-2, baseline LDH, age, sex, and the type and number of prior therapy). However, for women above 50 years of age, the data supporting an OS benefit of ipilimumab treatment were limited. The efficacy of ipilimumab for women above 50 years of age is therefore uncertain. As the subgroups analysis includes only small numbers of patients, no definitive conclusions can be drawn from these data. Median and estimated rates of OS at 1 year and 2 years are presented in Table 4.

TABLE 4

| Overall survival in MDX010-20 | | |
|---|---|---|
|  | Ipilimumab 3 mg/kg n = 137 | gp100[a] n = 136 |
| Median Months (95% CI) | 10 months (8.0, 13.8) | 6 months (5.5, 8.7) |
| OS at 1 year % (95% CI) | 46% (37.0, 54.1) | 25% (18.1, 32.9) |
| OS at 2 years % (95% CI) | 24% (16.0, 31.5) | 14% (8.0, 20.0) |

[a]gp100 peptide vaccine is an experimental control.

In the ipilimumab 3 mg/kg monotherapy group, median OS was 22 months and 8 months for patients with SD and those with PD, respectively. At the time of this analysis, medians were not reached for patients with CR or PR. For patients who required re-treatment, the BORR was 38% (3/8 patients) in the ipilimumab monotherapy group, and 0% in the gp100 group. The disease control rate (DCR) (defined as CR+PR+SD) was 75% (6/8 patients) and 0%, respectively. Because of the limited number of patients in these analyses, no definitive conclusion regarding the efficacy of ipilimumab re-treatment can be drawn. The development or maintenance of clinical activity following ipilimumab treatment was similar with or without the use of systemic corticosteroids.

In accordance with the present invention, patients participating in a study such as described above may be treated with a glutamate modulating agent, e.g., riluzole or its prodrug BHV-4157 (2-Amino-N-{[methyl({[6-(trifluoromethoxy)-1,3-benzo thiazol-2-yl]carbamoyl}methyl)carbamoyl]methyl}acetamide). The treatment regimen using the glutamate modulating agent may, for example, be as identified described in Example 2.

Example 5

The following illustrates an example of how a glutamate modulator of the present invention may be used in combination therapy with KEYTRUDA® (pembrolizumab), available from Merck & Co., Inc., Whitehouse Station, NJ, USA. For additional information, please see HIGHLIGHTS OF PRESCRIBING INFORMATION for KEYTRUDA® (pembrolizumab) for injection, for intravenous use KEYTRUDA® (pembrolizumab) injection, for intravenous use (uspi-mk3475-iv-1703r007) ("KETRUDA Package Insert").

In the Summary of Product Characteristics for KETRUDA, published by the European Medicines Agency, the following clinical study is disclosed. This study was not conducted by the Applicant, but is presented for illustrative purposes.

NSCLC—KEYNOTE-010: Controlled Trial of NSCLC Patients Previously Treated with Chemotherapy The safety and efficacy of pembrolizumab were investigated in KEYNOTE-010, a multicentre, openlabel, controlled study for the treatment of advanced NSCLC in patients previously treated with platinum-containing chemotherapy. Patients had PD-L1 expression with a ≥1% TPS based on the PDL1 IHC 22C3 pharmDx™ Kit. Patients with EGFR activation mutation or ALK translocation also had disease progression on approved therapy for these mutations prior to receiving pembrolizumab. Patients were randomised (1:1:1) to receive pembrolizumab at a dose of 2 (n=344) or 10 mg/kg(n=346) every 3 weeks or docetaxel at a dose of 75 mg/m2 every 3 weeks (n=343) until disease progression or unacceptable toxicity. The trial excluded patients with autoimmune disease; a medical condition that required immunosuppression; or who had received more than 30 Gy of thoracic radiation within the prior 26 weeks. Assessment of tumour status was performed every 9 weeks. The baseline characteristics for this population included: median age 63 years (42% age 65 or older); 61% male; 72% White and 21% Asian and 34% and 66% with an ECOG performance status 0 and 1, respectively. Disease characteristics were squamous (21%) and non-squamous (70%); M1 (91%); stable brain metastases (15%) and the incidence of mutations was EGFR (8%) or ALK (1%). Prior therapy included platinum-doublet regimen (100%); patients received one (69%) or two or more (29%) treatment lines. The primary efficacy outcome measures were OS and PFS as assessed by blinded independent central review (BICR) using RECIST 1.1. Secondary efficacy outcome measures were ORR and response duration. Table 5 summarises key efficacy measures for the entire population (TPS≥1%) and for the patients with TPS≥50%.

TABLE 5

Response to pembrolizumab 2 or 10 mg/kg every 3 weeks in previously treated patients with NSCLC in KEYNOTE-010

| Endpoint | Pembrolizumab 2 mg/kg every 3 weeks | Pembrolizumab 10 mg/kg every 3 weeks | Docetaxel 75 mg/m$^2$ every 3 weeks |
|---|---|---|---|
| TPS 1% | | | |
| Number of patients | 344 | 346 | 345 |
| OS | | | |
| Number (%) of patients with event | 172 (50%) | 156 (45%) | 193 (56%) |
| Hazard ratio* (95% CI) | 0.71 (0.58, 0.88) | 0.61 (0.49, 0.75) | — |
| p-Value† | <0.001‡ | <0.001‡ | — |
| Median in months (95% CI) | | | |
| PFS§ | | | |
| Number (%) of patients with event | 266 (77%) | 255 (74%) | 257 (75%) |
| Hazard ratio* (95% CI) | 0.88 (0.73, 1.04) | 0.79 (0.68, 0.94) | — |
| p-Value† | 0.068 | 0.005 | — |
| Median in months (95% CI) | 3.9 (3.1, 4.1) | 4.0 (2.6, 4.9) | 4.0 (3.1, 4.2) |
| Overall response rate§ | | | |
| ORR %§ (95% CI) | 18% (14, 23) | 18% (15, 23) | 9% (7, 13) |
| Response duration§,#,P | | | |
| Median in months (range) | Not reached (0.7+, 20.1+) | Not reached (2.1+, 17.8+) | 6.2 (1.4+, 8.8+) |
| % ongoing | 73% | 72% | 34% |
| TPS | | | |
| Number of patients | 139 | 151 | 152 |
| OS | | | |
| Number (%) of patients with event | 58 (42%) | 60 (40%) | 86 (57%) |
| Hazard ratio* (95% CI) | 0.54 (0.38, 0.77) | 0.50 (0.36, 0.70) | — |
| p-Value† | <0.001‡ | <0.001‡ | — |
| Median in months (95% CI) | 14.9 (10.4, NA) | 17.3 (11.8, NA) | 8.2 (6.4, 10.7) |
| PFS | | | |
| Number (%) of patients with event | 89 (64%) | 97 (64%) | 118 (78%) |
| Hazard ratio* (95% CI) | 0.58 (0.43, 0.77) | 0.59 (0.45, 0.78) | — |
| p-Value† | <0.001‡ | <0.001‡ | — |
| Median in months (95% CI) | 5.2 (4.0, 6.5) | 5.2 (4.1, 8.1) | 4.1 (3.6, 4.3) |
| Overall response rate§ | | | |
| ORR %¶ (95% CI) | 30% (23, 39) | 29% (22, 37) | 8% (4, 13) |
| Response duration§,#,B | | | |
| Median in months (range) | Not reached (0.7+, 16.8+) | Not reached (2.1+, 17.8+) | 8.1 (2.1+, 8.8+) |
| % ongoing | 76% | 75% | 33% |

*Hazard ratio (pembrolizumab compared to docetaxel) based on the stratified Cox proportional hazard model
†Based on stratified Log rank test
‡Statistically significant based on a pre-specified α level adjustment
§Assessed by blinded independent central review (BICR) using RECIST 1.1
¶All responses were partial responses
Based on patients with a best overall response as confirmed complete or partial response
P Includes 30, 31 and 2 patients with ongoing responses of 6 months or longer in the pembrolizumab 2 mg/kg, pembrolizumab 10 mg/kg and docetaxel arms respectively
B Includes 22, 24 and 1 patients with ongoing responses of 6 months or longer in the pembrolizumab 2 mg/kg pembrolizumab 10 mg/kg and docetaxel arms respectively Efficacy results were similar for the 2 mg/kg and 10 mg/kg pembrolizumab arms. Efficacy results for OS were consistent regardless of the age of tumour specimen (new vs. archival) based on an intergroup comparison. In subgroup analyses, a reduced survival benefit of pembrolizumab compared to docetaxel was observed for patients who were never-smokers or patients with tumours harbouring EGFR activating mutations who received at least platinum-based chemotherapy and a tyrosine kinase inhibitor; however, due to the small numbers of patients, no definitive conclusions can be drawn from these data. The efficacy and safety of pembrolizumab in patients with tumours that do not express PD-L1 have not been established.

In accordance with the present invention, patients participating in a study such as described above may be treated with a glutamate modulating agent, e.g., riluzole or its prodrug BHV-4157 (2-Amino-N-{[methyl({[6-(trifluoromethoxy)-1,3-benzo thiazol-2-yl]carbamoyl}methyl)carbamoyl]methyl}acetamide). The treatment regimen using the glutamate modulating agent may, for example, be as identified described in Example 2.

Throughout this application, various publications are referenced by author name and date, or by patent number or patent publication number. The disclosures of these publications are hereby incorporated in their entireties by reference into this application in order to more fully describe the state of the art as known to those skilled therein as of the date of the invention described and claimed herein. However, the citation of a reference herein should not be construed as an acknowledgement that such reference is prior art to the present invention.

Those skilled in the art will recognize, or be able to ascertain using no more than routine experimentation, numerous equivalents to the specific procedures described herein. Such equivalents are considered to be within the scope of this invention and are covered by the following claims. For example, it is intended in accordance with the present invention that combination therapy using a glutamate modulating agent and an immunotherapeutic agent can be employed to treat cancers other than the specific cancers disclosed in the description and Examples herein. Further, glutamate modulating agents and immunotherapeutic agents other than those disclosed in the description and Examples herein can be employed. Furthermore, it is intended that specific items within lists of items, or subset groups of items within larger groups of items, can be combined with other specific items, subset groups of items or larger groups of items whether or not there is a specific disclosure herein identifying such a combination.

What is claimed is:

1. A method of treating cancer in a patient in need thereof, comprising administering to the patient a therapeutically effective amount of a glutamate modulator and an immunotherapeutic anti-cancer agent, wherein the glutamate modulator has the following formula:

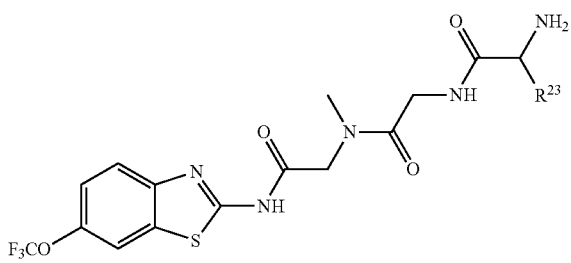

wherein $R^{23}$ is selected from the group consisting of H, $CH_3$, $CH_2CH_3$, $CH_2CH_2CH_3$, $CH_2CCH$, $CH(CH_3)_2$, $CH_2CH(CH_3)_2$, $CH(CH_3)CH_2CH_3$, $CH_2OH$, $CH_2OCH_2Ph$, $CH_2CH_2OCH_2Ph$, $CH(OH)CH_3$, $CH_2Ph$, $CH_2$(cyclohexyl), $CH_2$(4-OH-Ph), $(CH_2)_4NH_2$, $(CH_2)_3NHC(NH_2)NH$, $CH_2$(3-indole), $CH_2$(5-imidazole), $CH_2CO_2H$, $CH_2CH_2CO_2H$, $CH_2CONH_2$, and $CH_2CH_2CONH_2$, and
wherein the immunotherapeutic anti-cancer agent comprises a first checkpoint inhibitor selected from an anti-PD-1 antibody and an anti-PD-L1 antibody, and a second checkpoint inhibitor selected from an anti-PD-1 antibody and anti-CTLA-4 antibody, wherein the second checkpoint inhibitor is different from the first checkpoint inhibitor.

2. The method of claim 1, wherein the glutamate modulator has the following formula:

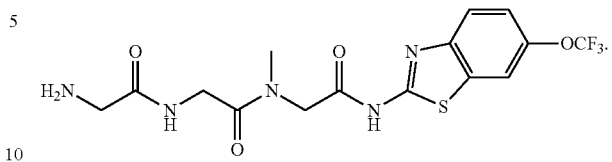

3. The method of claim 1, wherein the anti-PD-1 antibody is selected from nivolumab, pembrolizumab and pidilzumab.

4. The method of claim 1, wherein the anti-PD-L1 antibody is selected from BMS-936559, durvalumab, atezolizumab, avelumab, and MDX-1105.

5. The method of claim 1, wherein the anti-CTLA-4 antibody is selected from ipilimumab and tremelimumab.

6. The method of claim 1, wherein the glutamate modulator and the immunotherapeutic anti-cancer agent are capable of providing a Mouse Survival Ratio of at least 2.0 at day 60 ($MSR_{60}$).

7. A method for modulating glutamate in a patient being treated with an immunotherapeutic anti-cancer agent comprising contacting a glutamate receptor or a glutamate transporter in the patient with a glutamate modulator at a time proximate to the treatment with the immunotherapeutic anti-cancer agent,
wherein the glutamate modulator has the following formula:

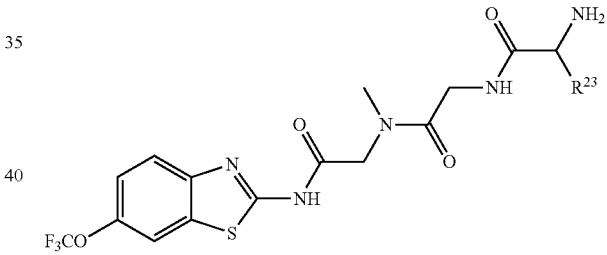

wherein $R^{23}$ is selected from the group consisting of H, $CH_3$, $CH_2CH_3$, $CH_2CH_2CH_3$, $CH_2CCH$, $CH(CH_3)_2$, $CH_2CH(CH_3)_2$, $CH(CH_3)CH_2CH_3$, $CH_2OH$, $CH_2OCH_2Ph$, $CH_2CH_2OCH_2Ph$, $CH(OH)CH_3$, $CH_2Ph$, $CH_2$(cyclohexyl), $CH_2$(4-OH-Ph), $(CH_2)_4NH_2$, $(CH_2)_3NHC(NH_2)NH$, $CH_2$(3-indole), $CH_2$(5-imidazole), $CH_2CO_2H$, $CH_2CH_2CO_2H$, $CH_2CONH_2$, and $CH_2CH_2CONH_2$,
wherein the immunotherapeutic anti-cancer agent comprises a first checkpoint inhibitor selected from an anti-PD-1 antibody and an anti-PD-L1 antibody, and a second checkpoint inhibitor selected from an anti-PD-1 antibody and anti-CTLA-4 antibody, wherein the second checkpoint inhibitor is different from the first checkpoint inhibitor, and
wherein the proximate time is within one week of the treatment with the immunotherapeutic anti-cancer agent.

8. The method of claim 7, wherein the proximate time is within one day of the treatment with the immunotherapeutic anti-cancer agent.

9. The method of claim 8, wherein the proximate time is within one hour of the treatment with the immunotherapeutic anti-cancer agent.

10. The method of claim 9, wherein the proximate time is within one minute of the treatment with the immunotherapeutic anti-cancer agent.

11. The method of claim 10, wherein the glutamate modulator has the following formula:

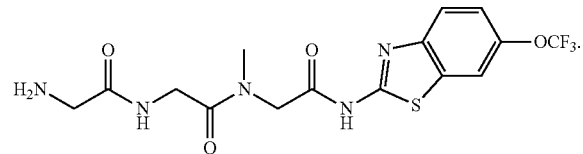 [SMILES: CN(CC(=O)Nc1nc2ccc(OC(F)(F)F)cc2s1)C(=O)CNC(=O)CN]

12. The method of claim 7, wherein the contacting of the glutamate receptor or glutamate transporter with the glutamate modulator is conducted before, concurrently, or after the treatment with the immunotherapeutic anti-cancer agent.

13. The method of claim 7, wherein the proximate time is within one (1) week of the treatment with the immunotherapeutic anti-cancer agent.

14. A method of sensitizing a patient afflicted with cancer being treated with an immunotherapeutic anti-cancer agent comprising administering to the patient a therapeutically effective amount of a glutamate modulator at a time proximate to the treatment with the immunotherapeutic anti-cancer agent,
wherein the glutamate modulator has the following formula:

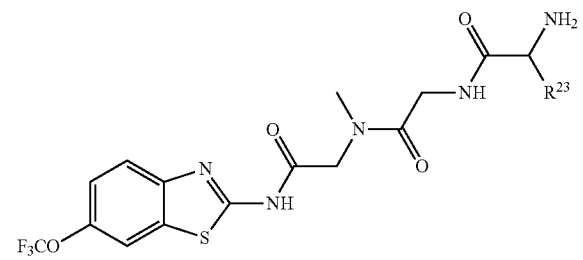

wherein $R^{23}$ is selected from the group consisting of H, $CH_3$, $CH_2CH_3$, $CH_2CH_2CH_3$, $CH_2CCH$, $CH(CH_3)_2$, $CH_2CH(CH_3)_2$, $CH(CH_3)CH_2CH_3$, $CH_2OH$, $CH_2OCH_2Ph$, $CH_2CH_2OCH_2Ph$, $CH(OH)CH_3$, $CH_2Ph$, $CH_2$(cyclohexyl), $CH_2$(4-OH-Ph), $(CH_2)_4NH_2$, $(CH_2)_3NHC(NH_2)NH$, $CH_2$(3-indole), $CH_2$(5-imidazole), $CH_2CO_2H$, $CH_2CH_2CO_2H$, $CH_2CONH_2$, and $CH_2CH_2CONH_2$, and
wherein the immunotherapeutic anti-cancer agent comprises a first checkpoint inhibitor selected from an anti-PD-1 antibody and an anti-PD-L1 antibody, and a second checkpoint inhibitor selected from an anti-PD-1 antibody and anti-CTLA-4 antibody, wherein the second checkpoint inhibitor is different from the first checkpoint inhibitor.

15. The method of claim 14, wherein the sensitization promotes enhanced anti-tumor efficacy.

16. The method of claim 15, wherein the enhanced anti-tumor efficacy is measured by an increased objective response rate or an increased response duration of the patient.

17. The method of claim 16, wherein the enhanced anti-tumor efficacy promotes an increase in the overall survival of the patient.

18. The method of claim 17, wherein the patient exhibits an overall survival of at least about 10 months after the initial administration of the immunotherapeutic anti-cancer agent.

19. The method of claim 17, wherein the overall survival of the is at least about 1.1 times, at least about 1.2 times, at least about 1.3 times, at least about 1.4 times, at least about 1.5 times, at least about 2.0 times, at least about 3.0 times, or at least about 3.0 times the overall survival of a patient treated with a therapeutically effective amount of an immunotherapeutic anti-cancer agent but without a glutamate modulator.

20. A method for improving a response in a patient afflicted with cancer being treated with an immunotherapeutic anti-cancer agent comprising administering to the patient in need thereof an effective amount of the immunotherapeutic anti-cancer agent and a glutamate modulator,
wherein the glutamate modulator has the following formula:

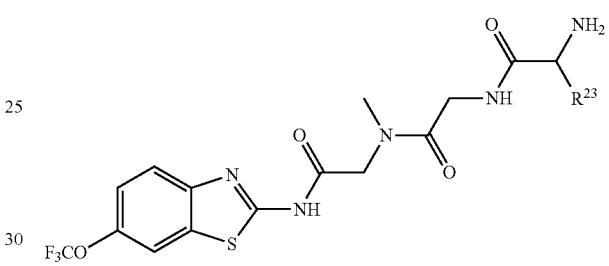

wherein $R^{23}$ is selected from the group consisting of H, $CH_3$, $CH_2CH_3$, $CH_2CH_2CH_3$, $CH_2CCH$, $CH(CH_3)_2$, $CH_2CH(CH_3)_2$, $CH(CH_3)CH_2CH_3$, $CH_2OH$, $CH_2OCH_2Ph$, $CH_2CH_2OCH_2Ph$, $CH(OH)CH_3$, $CH_2Ph$, $CH_2$(cyclohexyl), $CH_2$(4-OH-Ph), $(CH_2)_4NH_2$, $(CH_2)_3NHC(NH_2)NH$, $CH_2$(3-indole), $CH_2$(5-imidazole), $CH_2CO_2H$, $CH_2CH_2CO_2H$, $CH_2CONH_2$, and $CH_2CH_2CONH_2$, and
wherein the immunotherapeutic anti-cancer agent comprises a first checkpoint inhibitor selected from an anti-PD-1 antibody and an anti-PD-L1 antibody, and a second checkpoint inhibitor selected from an anti-PD-1 antibody and anti-CTLA-4 antibody, wherein the second checkpoint inhibitor is different from the first checkpoint inhibitor.

21. The method of claim 20, wherein the patient is additionally treated with an antibody selected from an anti-LAG3 antibody, an anti-CD137 antibody, an anti-KIR antibody, an anti-TGFp antibody, an anti-IL-10 antibody, an anti-B7-H4 antibody, an anti-Fas ligand antibody, an anti-CXCR4 antibody, an anti-mesothelin antibody, an anti-CD20 antibody, an anti-CD27 antibody, an anti-GITR antibody, an anti-OX40 antibody, or any combination thereof.

22. The method of claim 20, wherein the patient is additionally treated with radiation therapy, chemotherapy, a vaccine, a cytokine, a tyrosine kinase inhibitor, an anti-VEGF inhibitor, an IDO inhibitor, an IDO1 inhibitor, a TGF-beta inhibitor, or any combination thereof.

23. The method of claim 20, wherein the cancer is selected from melanoma cancer, renal cancer, prostate cancer, breast cancer, colon cancer, lung cancer, bone cancer, pancreatic cancer, skin cancer, cancer of the head or neck, cutaneous or intraocular malignant melanoma, uterine cancer, ovarian cancer, rectal cancer, cancer of the anal region, stomach cancer, testicular cancer, uterine cancer, carcinoma of the fallopian tubes, carcinoma of the endometrium, carcinoma of the cervix, carcinoma of the vagina, carcinoma of the vulva, Hodgkin's Disease, non-Hodgkin's lymphoma, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, chronic or acute leukemias including acute myeloid leukemia, chronic myeloid leukemia, acute lymphoblastic leukemia, chronic lymphocytic leukemia, solid tumors of childhood, lymphocytic lymphoma, cancer of the bladder, cancer of the kidney or ureter, carcinoma of the renal pelvis, neoplasm of the central nervous system (CNS), primary CNS lymphoma, tumor angiogenesis, spinal axis tumor, brain stem glioma, pituitary adenoma, Kaposi's sarcoma, epidermoid cancer, squamous cell cancer, T-cell lymphoma, environmentally induced cancers including those induced by asbestos, and any combinations thereof.

24. The method of claim 20, wherein the improved response is one or more of overall survival, quality of life, overall response rate, duration of response, progression free survival, patient reported outcome, minimal residual disease or immune response.

\* \* \* \* \*